United States Patent [19]
Tackles et al.

[11] Patent Number: 6,009,564
[45] Date of Patent: Jan. 4, 2000

[54] OPTICALLY CORRECTED GOGGLE

[75] Inventors: George Tackles, Capistrano Beach; Hans Moritz, San Clemente, both of Calif.; James H. Jannard, Spieden Island, Wash.; Ryan Saylor, Trabuco Canyon, Calif.

[73] Assignee: Oakley, Inc., Foothill Ranch, Calif.

[21] Appl. No.: 09/103,799

[22] Filed: Jun. 24, 1998

[51] Int. Cl.[7] ............................... A61F 9/02; G02C 3/02; G02C 7/02

[52] U.S. Cl. ............................... 2/436; 351/62; 351/158; 359/646

[58] Field of Search ............................... 2/435, 436, 437, 2/426, 427, 431, 432, 439, 442, 443, 447; 351/41, 44, 62, 158, 159, 170, 175; 359/646, 717

[56] References Cited

U.S. PATENT DOCUMENTS

| | | |
|---|---|---|
| D. 288,980 | 3/1987 | Pernicka . |
| D. 360,488 | 7/1995 | Cardinal . |
| D. 365,591 | 12/1995 | Jannard et al. . |
| D. 369,375 | 4/1996 | Jannard et al. . |
| 1,332,410 | 3/1920 | Potts . |
| 1,354,040 | 9/1920 | Hammon . |
| 1,536,828 | 5/1925 | Drescher . |
| 1,619,341 | 3/1927 | Gagnon . |
| 1,697,030 | 1/1929 | Tillyer . |
| 1,741,536 | 12/1929 | Rayton . |
| 1,910,466 | 5/1933 | Glancy . |
| 1,942,400 | 1/1934 | Glancy . |
| 2,406,608 | 8/1946 | Joyce . |
| 2,442,849 | 6/1948 | Glazer . |
| 2,615,162 | 10/1952 | Christensen et al. . |
| 2,709,256 | 5/1955 | Baratelli . |
| 2,928,097 | 3/1960 | Neufeld . |
| 3,055,256 | 9/1962 | Andresen, Jr. . |
| 3,377,626 | 4/1968 | Smith . |
| 3,409,909 | 11/1968 | Scott et al. . |
| 3,505,680 | 4/1970 | Ring . |
| 3,586,448 | 6/1971 | Beasse . |

(List continued on next page.)

FOREIGN PATENT DOCUMENTS

| | | |
|---|---|---|
| 0 456 321 | 5/1949 | Canada . |
| 0 121 018 A2 | 10/1984 | European Pat. Off. . |
| 0 446 698 A2 | 9/1991 | European Pat. Off. . |
| 2 500 176 | 8/1982 | France . |
| 2 626 086 | 7/1989 | France . |
| 2 688 322 | 9/1993 | France . |
| 2 740 231 | 4/1997 | France . |
| 38 17 850 A1 | 7/1989 | Germany . |
| 2 278 459 | 11/1994 | United Kingdom . |

OTHER PUBLICATIONS

Declaration of Alan W. Reichow (including exhibits).
Declaration of William D. Noonan (including exhibits).
Declaration of James H,. Jannard (Including exhibits).
Matsuura and Thompson, "The Consumers Choice in Athletic Eyewear", Doctoral Thesis, Pacific University College of Optometry, May 1983.

*Primary Examiner*—Peter Nerbun
*Attorney, Agent, or Firm*—Knobbe, Martens Olson & Bear, LLP

[57] ABSTRACT

A goggle is provided with double unitary lenses, separated by an insulating space to reduce fogging. At least one of the lenses is tapered to reduce prismatic distortion through the lens in an as-worn orientation. In an exemplary goggle, the tapering of one lens compensates for prismatic distortion and/or astigmatism introduced by the other of the lenses. The lenses are mounted in a goggle frame in a predetermined orientation with respect to a wearer's normal lines of sight. In one embodiment, the optical centerline or axis of the double lens system is aligned to be parallel with the wearer's normal lines of sight in the as-worn orientation. Method of manufacturing such lenses is also provided. The illustrated goggle defines an enclosed space between the inner lens and the wearer's face when worn, but includes ventilation to the enclosed space to allow moisture to escape.

23 Claims, 13 Drawing Sheets

U.S. PATENT DOCUMENTS

| | | |
|---|---|---|
| 3,591,864 | 7/1971 | Allsop . |
| 3,601,813 | 8/1971 | Alieo . |
| 4,271,538 | 6/1981 | Montesi et al. . |
| 4,443,893 | 4/1984 | Yamamoto . |
| 4,447,914 | 5/1984 | Jannard . |
| 4,571,748 | 2/1986 | Carroll et al. . |
| 4,682,007 | 7/1987 | Hollander . |
| 4,736,466 | 4/1988 | Kallstrom . |
| 4,737,918 | 4/1988 | Langlois et al. . |
| 4,867,550 | 9/1989 | Jannard . |
| 5,056,156 | 10/1991 | Kosmo et al. . |
| 5,131,101 | 7/1992 | Chin . |
| 5,138,494 | 8/1992 | Kurtin . |
| 5,220,689 | 6/1993 | Miller . |
| 5,287,562 | 2/1994 | Rush, III . |
| 5,347,323 | 9/1994 | Wilson . |
| 5,390,369 | 2/1995 | Tubin . |
| 5,410,763 | 5/1995 | Bolle . |
| 5,428,411 | 6/1995 | Kopfer . |
| 5,648,832 | 7/1997 | Houston et al. . |
| 5,689,323 | 11/1997 | Houston et al. . |
| 5,802,622 | 9/1998 | Baharad et al. ......... 2/436 X |
| 5,815,848 | 10/1998 | Jarvis ...................... 2/425 X |

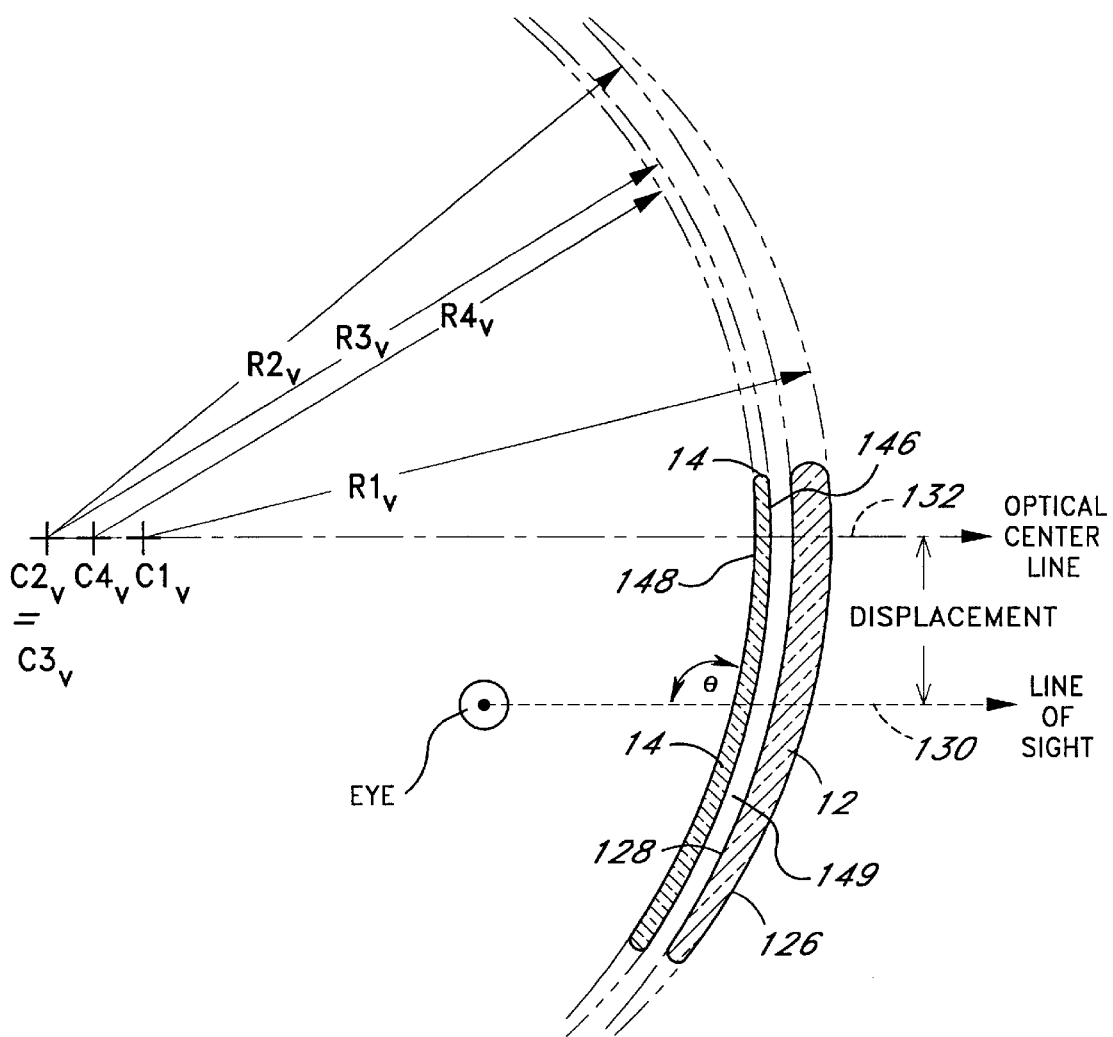

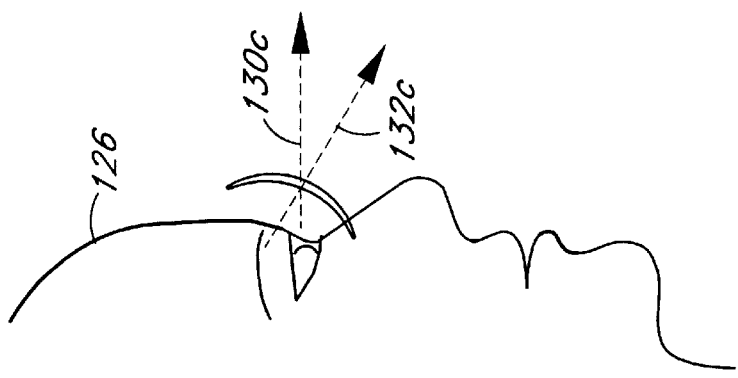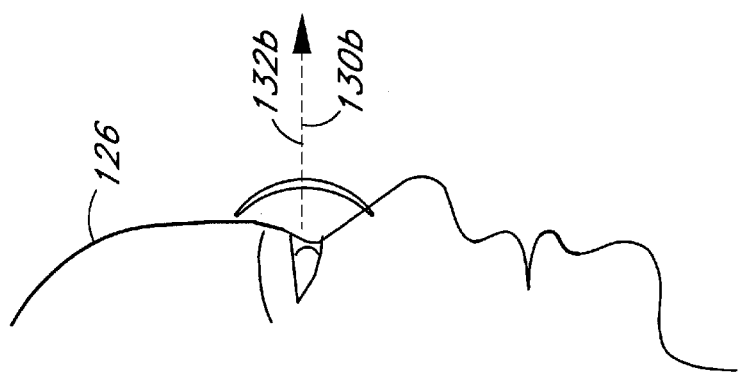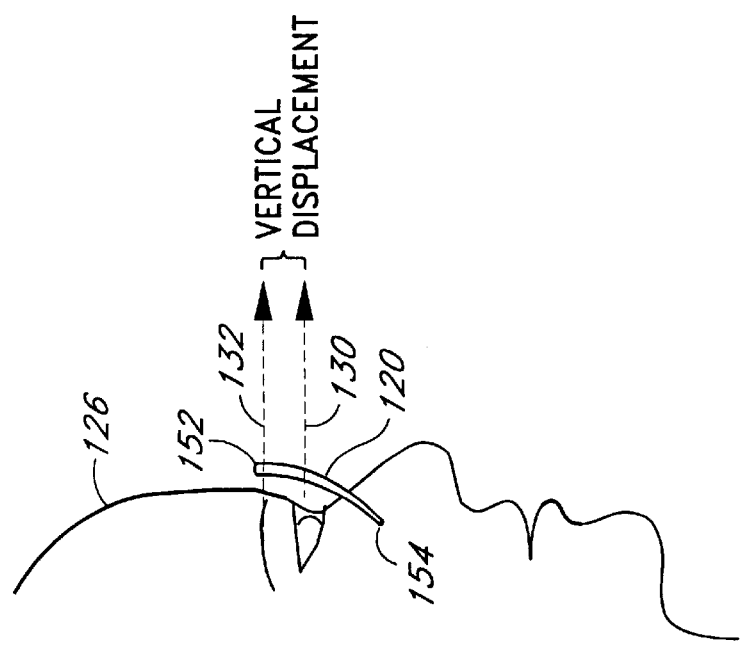

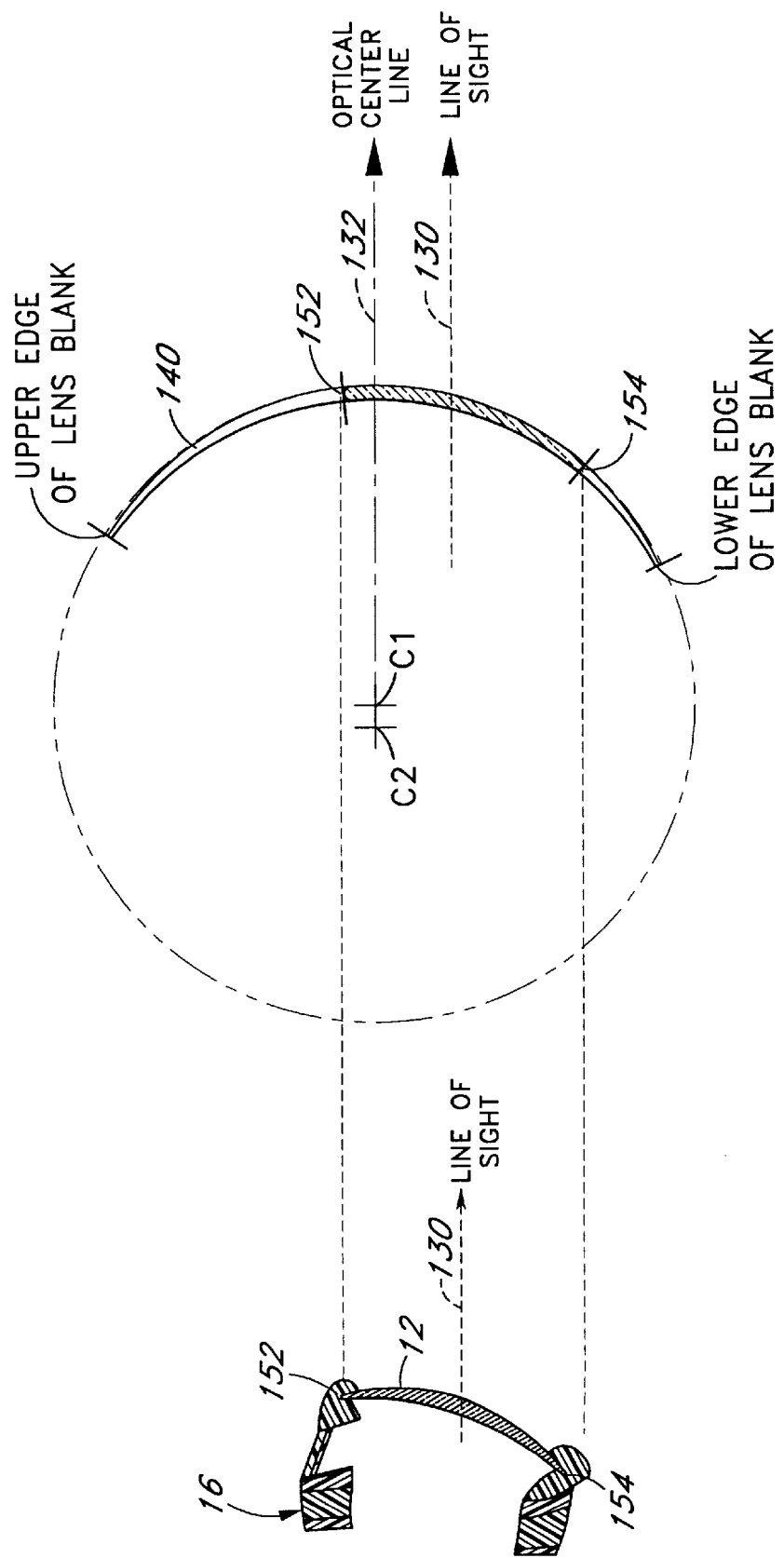

OPTICALLY CORRECTED GOGGLE

FIELD OF THE INVENTION

The present invention relates generally to lenses used in eyewear, and more particularly to a goggle lens system configured and oriented to reduce optical distortion and lens fogging.

BACKGROUND AND SUMMARY OF THE INVENTION

A wide variety of improvements have been made in recent years in the eyewear field, particularly with respect to eyewear intended for use in active sports or as fashion sunglasses. These improvements have been incorporated into eyewear having a unitary lens, such as the "Blades®" design (Oakley, Inc.) the "M Frame®" line (Oakley, Inc.), and the "Zero®" line also produced by Oakley, Inc. These eyewear designs accomplish a variety of functional advantages, such as maximizing interception of peripheral light, reducing optical distortion and increasing the wearer's comfort level, compared to previous active sport eyewear.

The unitary lens of the "Blades®" eyewear incorporates the cylindrical geometry disclosed, for example, in U.S. Pat. No. 4,859,048, issued to Jannard This geometry allows the lens to closely conform to the wearer's face and intercept light, wind, dust, etc. from directly in front of the wearer (anterior direction) and peripherally (lateral direction). See also U.S. Pat. No. 4,867,550 to Jannard (toroidal lens geometry).

Although the early unitary lens systems provided a full side-to-side range of vision and good lateral eye protection, the potential for optical distortion still exists. In a unitary lens system, for example, the angle of incidence from the wearer's eye to the posterior lens surface changes as the wearer's sight line turns in either the vertical or horizontal planes. This results in disparate refraction between light entering closer to the front of the lens and peripheral light entering at the lateral ends. To address this source of prismatic distortion, U.S. Pat. No. 4,859,048 discloses tapering the thickness of the lens from the medial portion toward the lateral edge.

Unitary lens protective helmet shields are subject to the same sources of optical distortion. A wide variety of helmet shields are known for such activities as motorcycle riding, football, lacrosse, hockey and the like. While the state of the art in each of these applications has generally achieved the desired level of physical eye protection, the current products generally still exhibit relatively high prismatic distortion and sometimes also power and/or astigmatism.

Another class of eyewear known as goggles often employ unitary lenses. Goggle applications include skiing, motocross, underwater diving masks, and a variety of industrial safety applications such as welding and for power equipment operators. Typically, goggles offer sealed protection to the eyes and adjacent areas of the wearer's face against particulate matter or water, without providing full head protection. As with helmets, goggle designs have tended to achieve good protection at the expense of introducing prismatic distortion, power and/or astigmatism.

One additional factor which affects vision through goggles is fogging. Because the wearer's face is usually warmer than the surrounding atmosphere for most applications (particularly for skiing and diving), the goggle lens is often colder than air trapped between the wearer's face and the lens. Moisture in the trapped air (e.g., from the wearer's sweat) thus tends to condense upon the inside of a goggle lens. Indeed, in extremely cold conditions, as often encountered in skiing applications, condensed moisture can even freeze upon the lens, clouding vision considerably.

One solution to this problem is to vent moisture from the wearer's side of the goggle lenses to the outside of the lens. This solution is, of course, impractical for diving applications. Even for skiing, however, providing ventilation risks allowing wind, snow, hard ice particles, etc. to enter the goggles, counter to the purpose for the goggles. Accordingly, any ventilation for the purpose of defogging must be minimized to prevent injury to the wearer.

Another solution to the problem of fogging in goggles is to provide insulation between the lens surface closest to the wearer's face and the cold outside atmosphere. Double lens structures, having spaced inner and outer lenses, provide such insulation in many goggle designs. Exemplary prior art double lens goggles are disclosed in U.S. Pat. Nos. 3,377,626; 3,591,864; and 4,571,748. The double lens insulated structure has also been applied to dual lens goggles, with each of a left lens and right lens including inner and outer lenses, as disclosed in U.S. Pat. No. 5,428,411.

While ventilation and/or double lens structures may reduce fogging, such structures do not address and may exacerbate optical distortion through the lenses. Accordingly, there remains a need for a nonprescription goggle which can protect a wearer's eyes from harmful light, wind and particles while at the same time minimize optical distortion throughout both a vertical and horizontal angular range of vision.

SUMMARY OF THE INVENTION

There is provided in accordance with one aspect of the present invention, an optically corrected, non-prescription double lens goggle. The goggle includes an inner lens with a first curved configuration and an outer lens with a second curved configuration. Both inner and outer lenses are supported within a goggle frame, with the inner lens spaced behind the outer lens by an insulating space. At least one of the inner and outer lenses have a thickness which is tapered to reduce prismatic distortion through the goggle. The reduced distortion is measured relative to an uncorrected double lens goggle having the same general curvatures and interlens spacing, but with uniformly thick lenses.

In accordance with another aspect of the present invention, a double lens goggle is provided. The goggle includes a goggle frame configured to fit on a wearer's head in an as-worn orientation. A first curved unitary lens is mounted to the goggle frame for extending across the wearer's left and right eyes in the as-worn orientation. This lens has a first prismatic effect on the wearer's vision in the as-worn orientation. A second curved unitary lens is also mounted to the goggle frame, spaced from the first lens to define an insulated space between the two lenses. The second lens has a second prismatic effect on the wearer's vision which substantially compensates for the first prismatic effect.

In accordance with another aspect of the present invention, a ski goggle is provided with a unitary lens. The lens exhibits no more than about ⅛ diopter prismatic distortion, and no more than about ⅛ diopter refractive power. A goggle frame supports the lens upon the wearer's head in the as-worn orientation. When worn, the frame defines an enclosed space between the lens and the wearer's head. A vent through the front side of the goggle communicates air to the enclosed space in the as-worn orientation.

BRIEF DESCRIPTION OF THE DRAWINGS

FIG. 15 is a schematic vertical cross-section of the double lens system of FIG. 13, constructed and oriented in the vertical dimension in accordance with the preferred embodiment.

FIGS. 15A–15E are right side elevational views of lenses of various configurations and orientations relative to a wearer.

FIG. 15A illustrates the profile of a properly configured and oriented lens for use in eyewear having downward rake, in accordance with an embodiment of the present invention.

FIG. 15B illustrates the profile of a centrally oriented lens with no rake.

FIG. 15C illustrates a lens exhibiting downward rake but which is not configured and oriented to minimize prismatic distortion for the straight ahead line of sight.

FIG. 15D illustrates a lens exhibiting upward rake but which is not configured and oriented to minimize prismatic distortion for the straight ahead line of sight.

FIG. 15E illustrates the profile of a properly configured and oriented lens for use in eyewear having upward rake, in accordance with an embodiment of the present invention.

FIG. 17 schematically illustrates the projection of the lens vertical profile from a desired orientation within a goggle frame to the lens blank, in accordance with a preferred embodiment of the present invention.

DETAILED DESCRIPTION OF THE PREFERRED EMBODIMENTS

Although preferred embodiments will be discussed below in terms of double lens goggles particularly adapted for snow skiing applications, it will be understood by those having ordinary skill in the art that the invention is also be applicable to other goggle applications. Furthermore, while the preferred embodiments have particular lens surface geometries, front elevational shapes and orientations advantageous to the skiing application, the skilled artisan will readily find application for the principles disclosed herein to lenses having different geometries and orientations in the as-worn position beyond those illustrated herein. For example, each orbital of a dual lens goggle may also include a double lens structure in accordance with the present disclosure.

Figure 7:
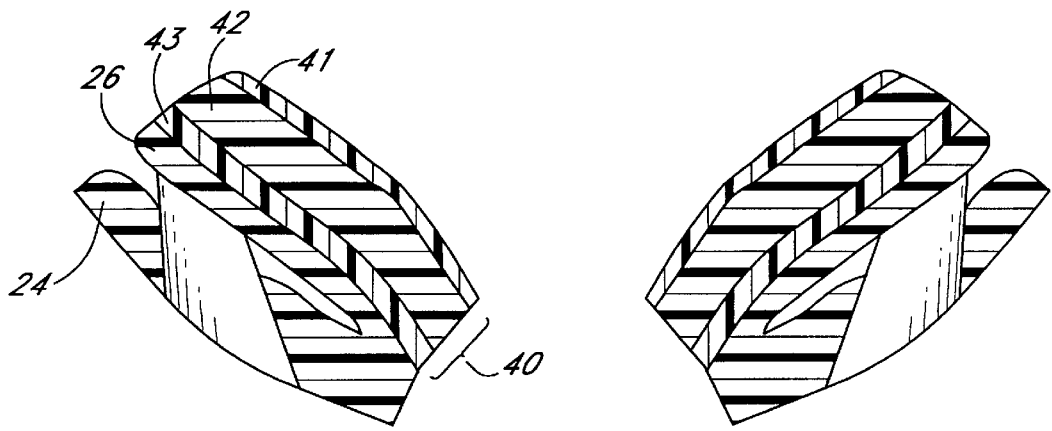
FIG. 7 is a horizontal cross-sectional view of a lower portion of the goggle, taken along lines 7—7 of FIG. 2.
Figure 8:
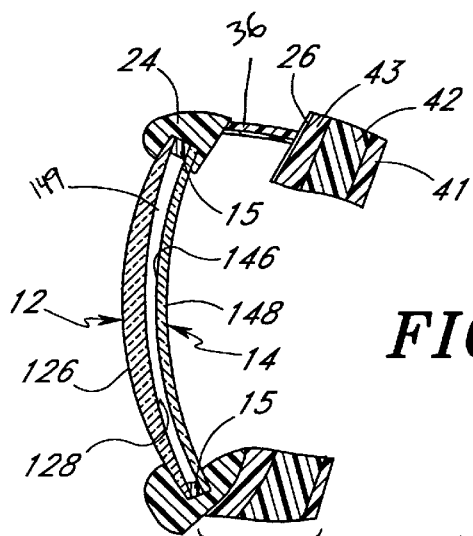
FIG. 8 is a vertical cross-sectional view taken along lines 8—8 of FIG. 2.
Figure 9:
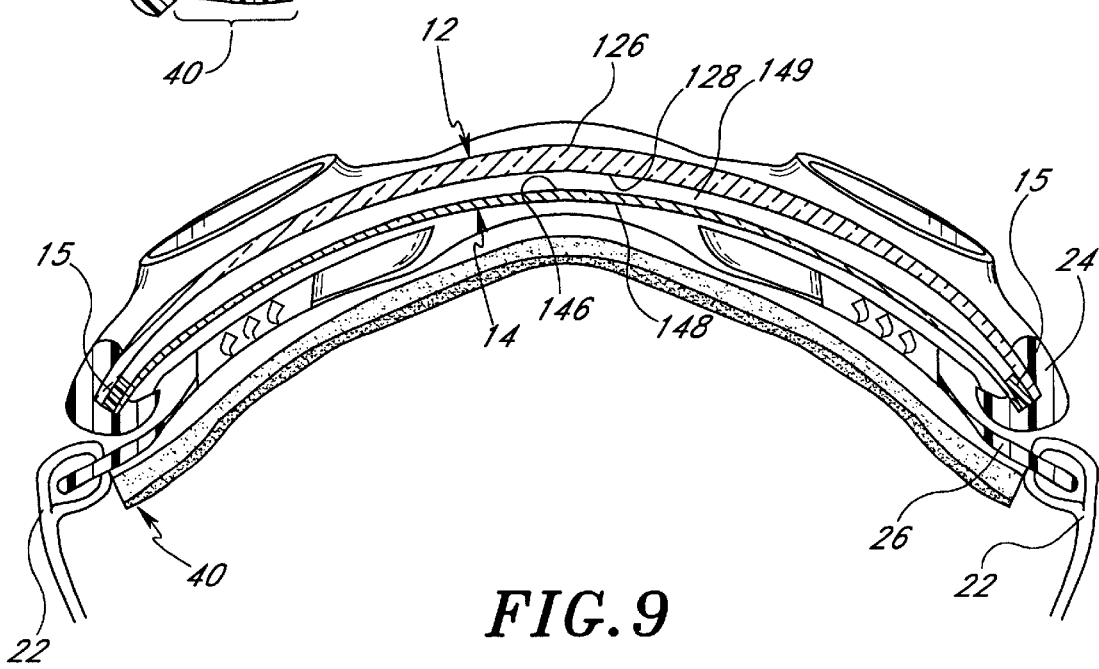
FIG. 9 is a horizontal cross-section view of a central portion of the goggle, taken along lines 9—9 of FIG. 2.

Referring to FIGS. 1 to 9, there is illustrated a ski goggle 10, constructed in accordance with an embodiment of the present invention. A first, front or outer lens 12 can be seen in the view of FIGS. 1 to 3. The goggle 10 further includes a second, rear or inner lens 14, separated from the outer lens 12 by a continuous gasket 15 around the perimeter of the lenses 12, 14 (FIGS. 8 and 9). Each of the illustrated lenses 12, 14 are unitary lenses, configured to extend across the vision of both eyes in an as-worn orientation upon a wearer's head. The lens configurations and orientations relative to one another and to the wearer are discussed in more detail below.

Mounting System

The goggle 10 further includes a mounting frame 16, configured to support the lenses 12, 14 on the wearer's head in the as-worn orientation. The illustrated frame 16 continuously bounds the edges of the lenses, surrounding and defining a unitary viewing window 18 (best seen from FIG. 2) across which the lenses 12, 14 extend While such a configuration is preferred for ski goggles, it is not essential for providing many of the advantages of the preferred embodiment. In other arrangements, a frame may bound only the bottom edges of the lenses or only the top edges. Alternatively, a frame can bound any other portions of the lenses as will be evident to those of skill in the art. Frameless eyewear can also be constructed in accordance with certain aspects of the present invention. Preferably, though, the lens edges are continuously bounded by the frame 16 as shown.

When worn, the viewing window 18 defined by the frame 16 should at least extend across the wearer's normal straight ahead lines of sight from each eye, and preferably substantially across the wearer's peripheral zones of vision. As used herein, the wearer's normal lines of sight shall refer to lines projecting straight ahead of the wearer's eyes, with substantially no angular deviation in either the vertical or horizontal planes. Due to variations in the way a particular eyeglass will sit on the heads of different wearers, it may be convenient to reference theoretical normal straight ahead lines of sight which exhibit no vertical or horizontal deviation. Theoretical lines of sight can be standardized such as by reference to Alderson's head forms, as will be understood by those of skill in the art. Preferred orientations of the lenses 12, 14 with respect to the wearer's normal lines of sight will be better understood in light of FIGS. 13–17 and the accompanying descriptions below.

The frame 16 can comprise any of a variety of metals, composites or relatively rigid, molded thermoplastic materials which are well known in the art, and may be transparent or any of a variety of colors. The illustrated frame 16, however, is preferably constructed of a relatively flexible yet elastic material, which can deform to facilitate application to the wearer's head and return to the original molded shape to retain the lenses 12, 14 in the desired orientation. Flexibility also facilitates slight deviation from the standard Alderson's head form in order to customize fit to the actual wearer's face. An exemplary frame material comprises urethane, though other polymeric materials are known which can satisfy these needs. Injection molding, machining and other construction techniques are well known in the art.

Figure 1:
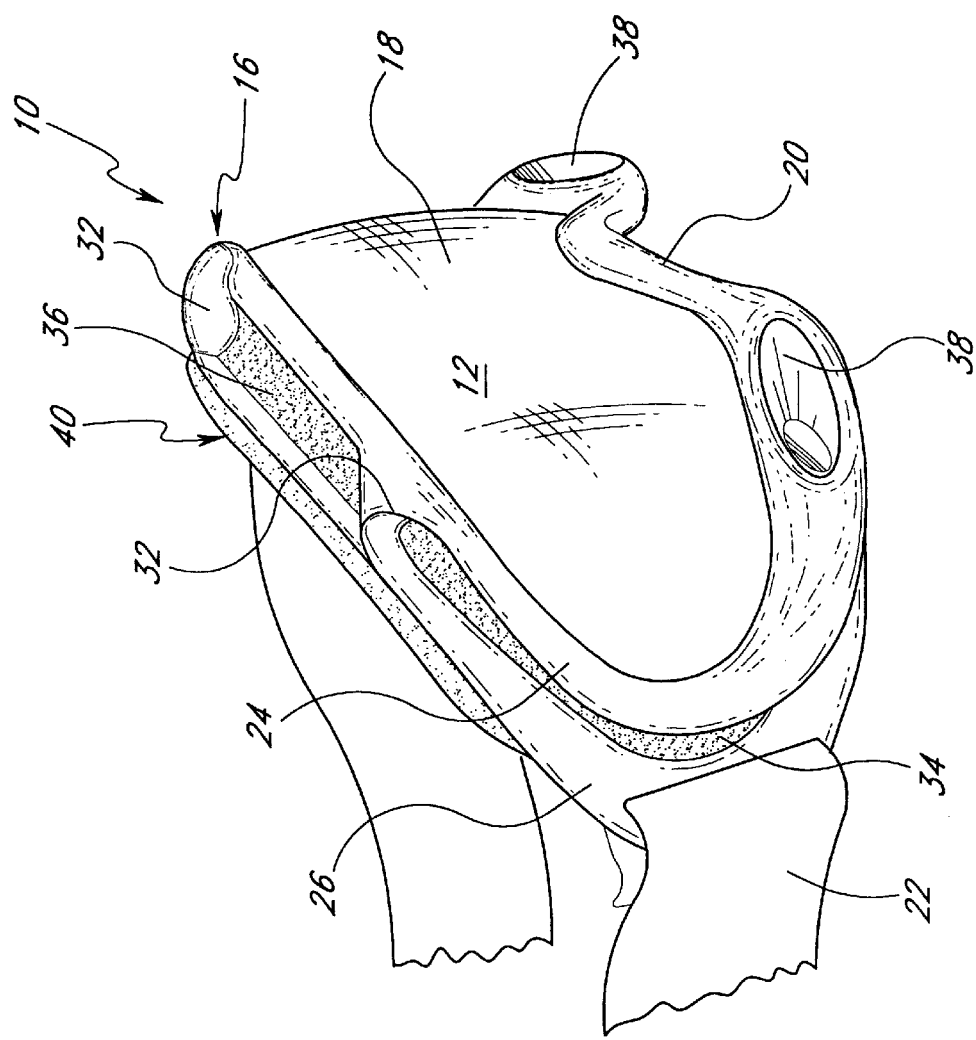
FIG. 1 is a perspective view of a single or double lens goggle incorporating taper corrected lenses made in accordance with an embodiment of the present invention.
Figure 2:
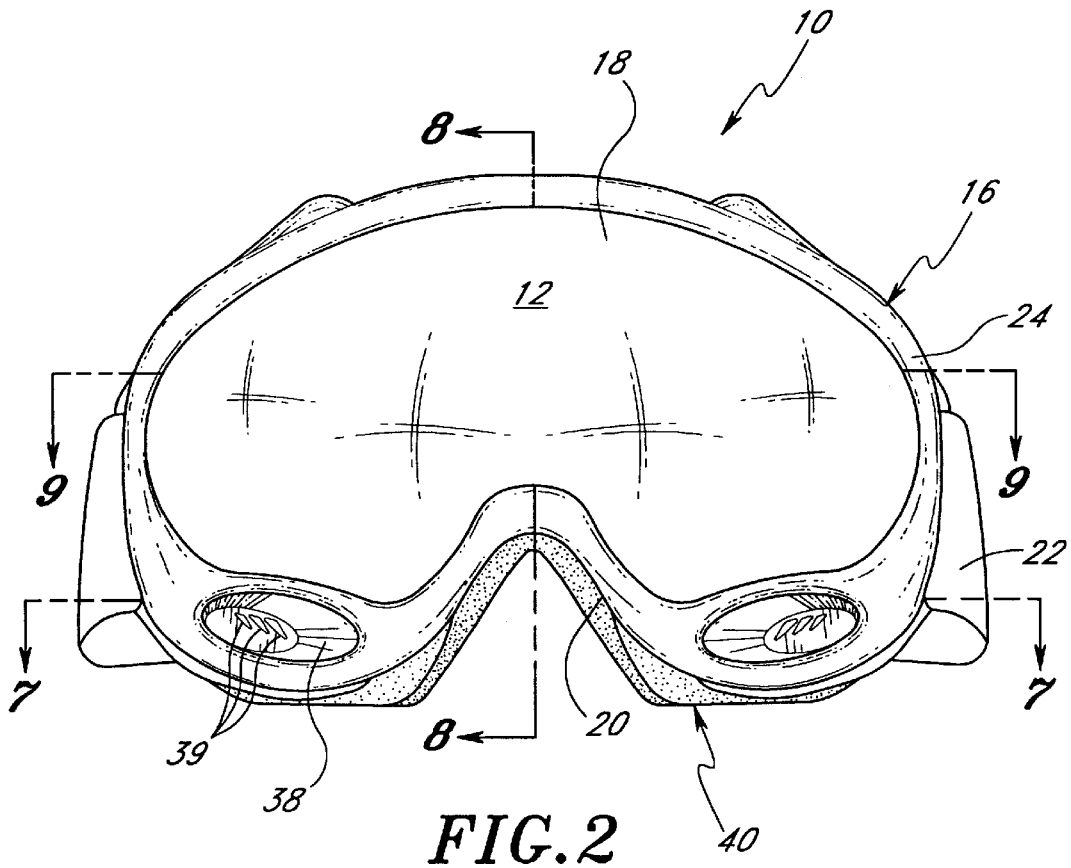
FIG. 2 is a front elevational view of the goggle of FIG. 1.
Figure 3:
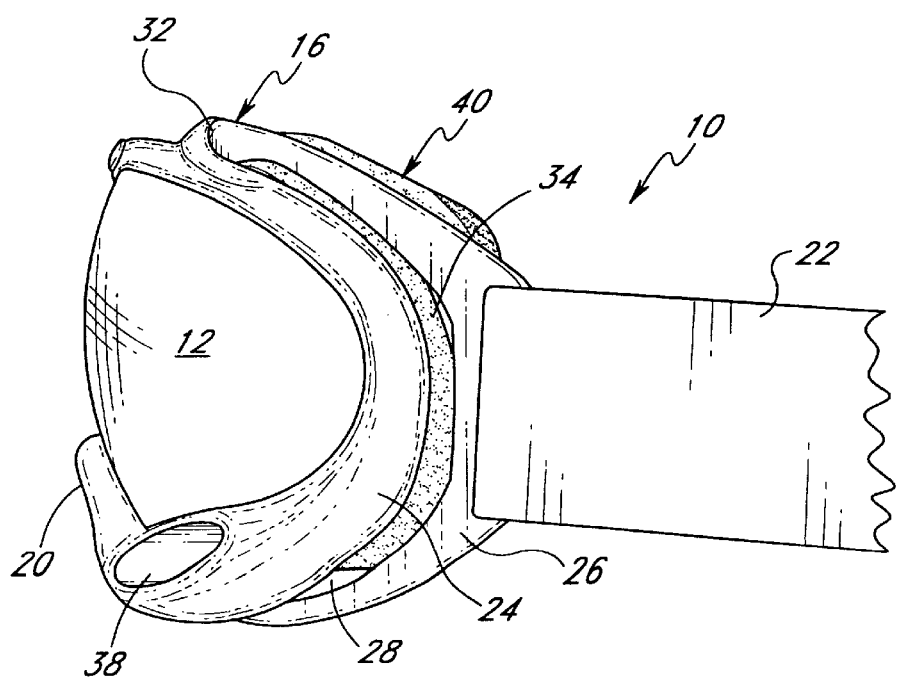
FIG. 3 is a side elevational view of the goggle of FIG. 1.

FIG. 2 illustrates a preferred shape for the viewing window 18 defined by the frame 16. Preferably, the bottom edge of the frame 16 includes a medial recess 20 shaped to rest upon the wearer's nose when worm. The height of the viewing window 18 above the medial recess 20 is preferably between about 1.5 inches and 2.5 inches, and is about 2.0 inches for the illustrated embodiment. In contrast, the height of the viewing window 18 preferably extends on either lateral side of the recess 20 to between about 2.0 inches and 4.0 inches, to provide a greater vertical range of vision to each of the wearer's eyes, and is about 2.7 inches for the illustrated embodiment A strap 22 is shown attached to each lateral side of the flame 16, preferably looped through slots provided at the lateral sides of the frame 16. Advantageously, the strap 22 is adjustable and comprises an elastic material to facilitate stretching over the wearer's head, and to facilitate pulling the frame 16 to conform against the wearer's face, as will be appreciated by the skilled artisan. It will be understood that, in other arrangements, the frame can be supported upon the wearer's head by multiple straps, by suspension from a helmet, or by a pair of earstems. Earstems can also attach directly to the lenses in a known fashion.

Figure 4:
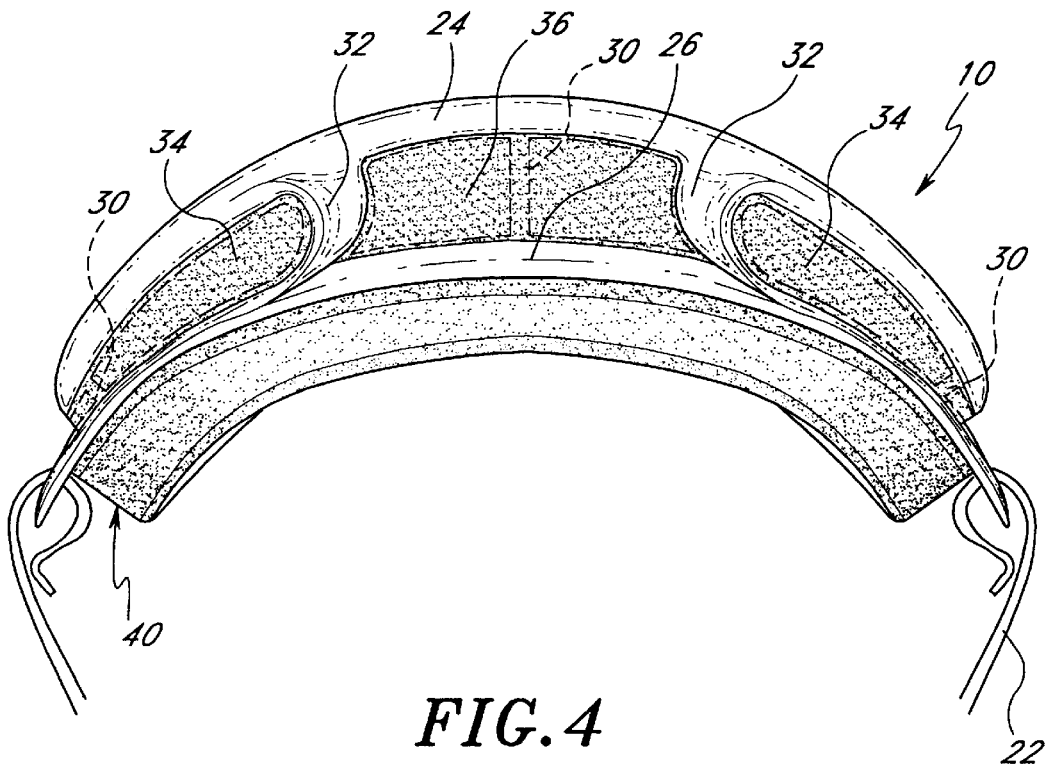
FIG. 4 is top plan view of the goggle of FIG. 1.
Figure 5:
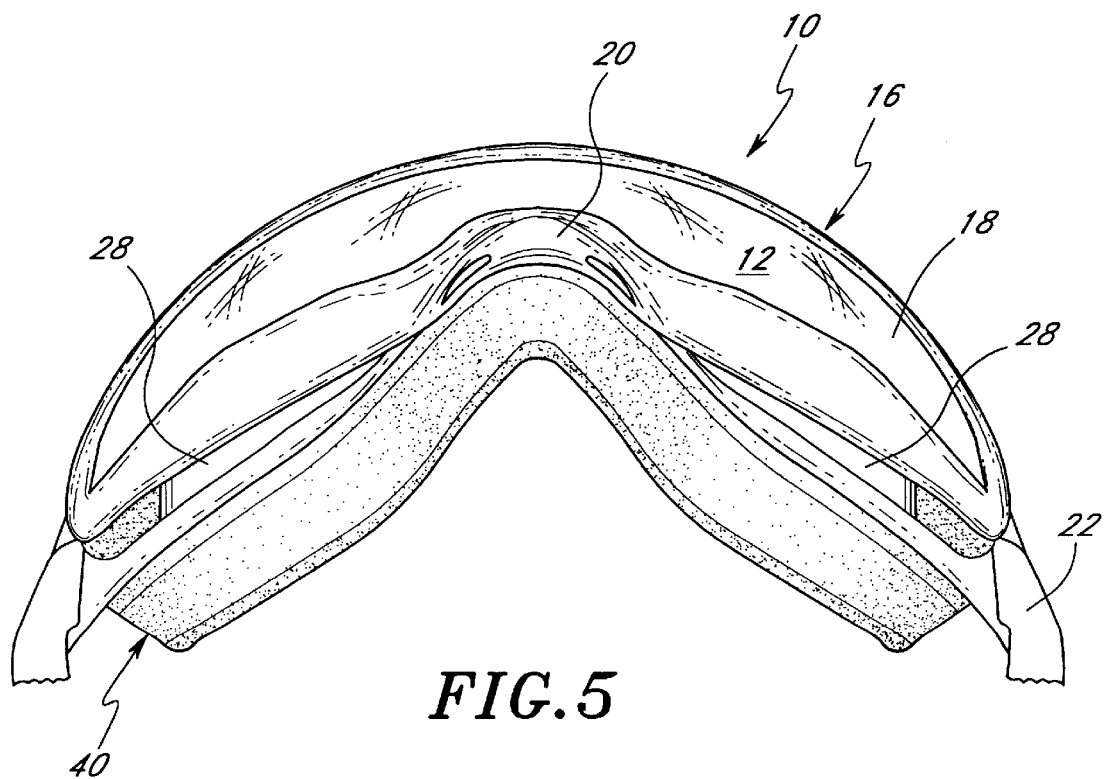
FIG. 5 is a bottom plan view of the goggle of FIG. 1.
Figure 6:
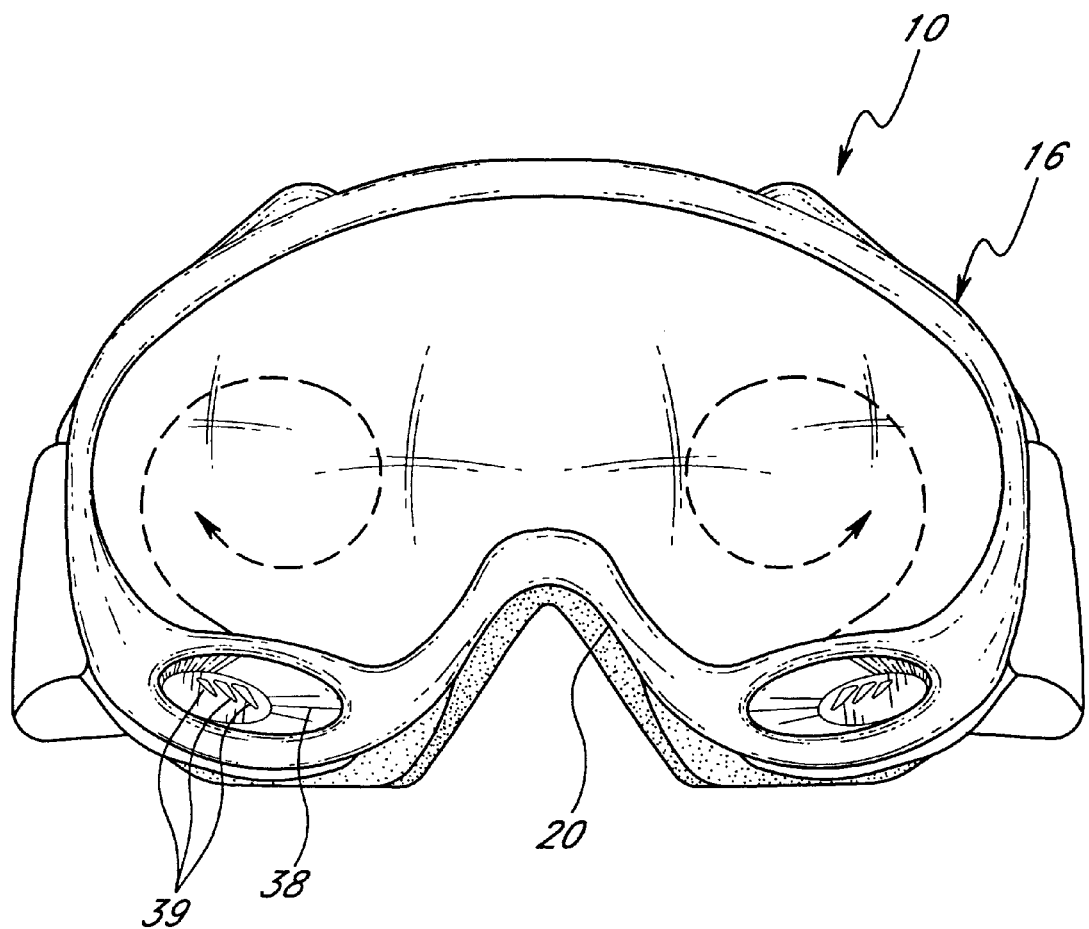
FIG. 6 is a front elevational view, similar to FIG. 2, but showing patterns of air circulation experienced within the goggle in use.

The illustrated frame 16 has a double frame construction, including an outer or front frame portion 24, bounding the lenses 12, 14, and an inner or rear frame portion 26 spaced behind the front frame portion 24. In the illustrated embodiment, the front frame portion 24 is spaced by about 3/4 inch from the rear frame portion 26 at the top of the goggle 10 (FIG. 4). The spacing tapers slightly down the height of the goggle 10 such that the portions 24, 26 merge at the bottom of the goggle 10 (FIG. 4) at vent bottom surfaces 28 to the left and to the right of the medial recess 20. Each of the vent bottom surfaces 28 are upwardly recessed relative to the bottom surfaces of the front frame portion 24 and the rear frame portion 26. The illustrated frame portions 24, 26 are also connected to one another by a plurality of thin ribs 30 (FIG. 5) and two relatively thicker bridge portions 32 at or near the top portion of the frame 16. The illustrated bridge portions 32 advantageously have a curved configuration, with a concave side facing laterally away from the central medial portion of the frame 16.

The double frame structure thus defines relatively open lateral portions (FIG. 3) and a relatively open top portion (FIG. 4) between the bridge portions 32. As illustrated, these open portions are covered by lateral membranes 34 and a top membrane 36, respectively. Each of these membranes 34, 36 preferably comprise a thin, air permeable material which can keep particles of snow or ice out, while allowing water vapor to pass through. An exemplary membrane material comprises an open cell polyurethane foam.

Referring again to FIGS. 1 to 3, at the bottom portion of the frame 16, laterally on either side of the medial recess 20, the frame includes a pair of front air intakes or vents 38, on the same side of the goggle 10 as the viewing window 18. Each front vent 38 comprises a passage open at the front of the frame 16, extending between the front frame portion 24 and the rear frame portion 26, and opening upwardly into the space defined between the two frame portions 24, 26. The illustrated front vents 38 each include a plurality of slots 39 opening upwardly from the interior of the vents. Desirably, the illustrated vents 38 extend from a relatively wide opening at the front of the frame 16 to a relatively more narrow rear portion.

The vents 38, including the slots 39, are configured to direct air laterally and upwardly into an enclosed space defined between the inner lens 14 (FIGS. 8 and 9) and wearer's face in the as-worn condition. Advantageously, this configuration causes the circular air flow pattern indicated by the arrows in FIG. 6, before the air is exhausted through one of the membranes 34, 36. It has been found that this circulation reduces lens fogging in operation. While not illustrated, each vent 38 preferably includes an air permeable plug (comprising, e.g., polyurethane foam) to prevent ice particles and the like from entering through the vent 38 while dampening air flow to a desired level.

The rear surface of the rear frame portion 26 is preferably lined with a cushioning material 40. As best seen from the cross-sectional views of FIGS. 7 and 8, the cushioning material 40 preferably comprises an inner layer 41, an intermediate layer 42, and a outer layer 43. The inner layer 41 preferably comprises a soft, matted or woven fiber to prevent chaffing the wearer's face, such as Polartec™, available from Malden Mills, Lawrence, Mass. The intermediate layer preferably comprises a resilient, deformable material such as an open cell polyurethane foam, while the outer layer 42 preferably can comprise a relatively more dense foam material which is readily adhered to the material of the rear frame portion 26.

In addition to defining an enclosed space relatively safe from particulate entry while permitting ventilation of moisture from this enclosed space, the illustrated double frame structure also absorbs any deformation required to fit a non-standard head form. The frame 16 is preferably designed to establish a desired predetermined orientation between the lenses 12, 14 and a standard head form (such as Alderson's head forms), thereby establishing a relation between the lenses 12, 14 and standard normal lines of sight. Not all wearers, however, conform to the standard head form.

The preferred goggle addressees this problem by providing the double frame structure. In particular, the rear frame portion 26 and the attached cushioning layer 40 are more flexible than the front frame portion 24, which is also reinformed by the lenses 12, 14. The rear frame portion 26 can thus flex while the cushioning layer 40 deforms somewhat to conform to an actual individual's face, which may deviate somewhat from the standard head form. Deviation from the standard head form is mostly, if not entirely, accommodated by the rear frame portion 26 and cushioning layer 40. The relatively more rigid front frame portion 24 tends to retain the desired orientation to the actual wearer's normal lines of sight. The frame 16 thus advantageously provides customized fit to an individual's face with minimal to no deviation from the desired predetermined orientation between the wearer's normal lines of sight and the lenses 12, 14.

Furthermore, the illustrated ribs 30 and particularly the curved bridge portions 32 are configured to maintain a symmetrical relationship between the viewing window 18 and the wearer's normal lines of sight, even when the rear frame portion 26 flexes somewhat to accommodate a non-standard head form. Accordingly, any imbalance in the optical effect experienced by the left and right vision of the wearer is minimized.

Lens Construction

Curvatures in General

FIGS. 7 and 8 show the vertical and horizontal profiles, respectively, of the preferred lenses 12, 14. As illustrated, each lens is curved, preferably in a regular fashion, in each of the horizontal and vertical dimension. By convention in the industry, the curvature of a lens can be expressed in terms of a base value, such that the radius (R) in millimeters of the anterior (front) surface of the lens is equal to 530 divided by the base curve, or $$R = \frac{530}{B} \quad (1)$$

In the illustrated embodiment, the anterior (front) surfaces of each of the outer lens 12 and inner lens 14 generally conform to the surfaces of toroids. Accordingly, the curvature of the preferred lenses can be characterized by horizontal and vertical radii of curvatures or base curves. By definition, if the horizontal and vertical radii on the same lens surface are equal, that lens surface has spherical geometry.

In the illustrated toroidal geometry lenses, the front surface of each lens 12, 14 is characterized by a horizontal radius of curvature $R_h$ and a vertical radius of curvature $R_v$. $R_h$ is preferably within the range of from about 2.00 inches to 4.00 inches, more preferably between about 2.75 inches and 3.50 inches, and most preferably is between about 3.1 inches and 3.3 inches. Desirably, the vertical radius $R_v$ exceeds the horizontal curvature $R_h$ by at least about 10% or 15%, such that each lens is flatter in the vertical dimension than in the horizontal dimension. Preferably, $R_v$ is about 1.1 to 4.0 times $R_h$, more preferably between about 1.5 to 3 times $R_h$. The radius of curvature in the horizontal dimension is thus preferably between about 4.0 inches and 6.0 inches, more preferably between about 4.8 inches and 5.1 inches. For the outer lens 12 of an exemplary goggle, $R_h$=3.2624 inches and $R_v$=5.046 inches. For the inner lens 14 of the same goggle, $R_h$=3.1631" and $R_v$=4.9138 inches.

Thickness Variation For Optical Correction

The foregoing radius dimensions represent the distance from an axis to the arc which defines the front, convex surface of the lens at issue. The lenses of the preferred embodiments, however, have sufficient thickness that they are not accurately defined as having only a single radius. Instead, the lens has a thickness or depth dimension along its entire arc length, in both horizontal and vertical dimensions, which causes the arc defined by the rear, concave surface to have a different radius than the radius of the front surface. Hence, where a lens has a substantially uniform thickness throughout, the radius of the rear surface is essentially equal to the difference between the radius of the front surface and the depth or thickness of the lens. Such a uniformly thick lens is said to have concentric surfaces, as will be understood by one of skill in the art. The thickness of the preferred lenses 12, 14 is discussed in more detail below.

As noted, the principal embodiments described herein are of constant radius in both horizontal and vertical cross-sections. A variety of lens configurations in both planes, however, are possible in conjunction with the present invention. Thus, for example, either the front or rear or both surfaces of a lens of the present invention can generally conform to a toroidal shape as shown in FIGS. 8 and 9. Alternatively, the surfaces of either or both of the inner and outer lenses can conform to a sphere, right circular cylinder, a frusto-conical, an elliptic cylinder, an ellipsoid, an ellipsoid of revolution, or any of a number of other three dimensional shapes. Regardless of the particular vertical or horizontal curvature of one surface, however, at least one of the other surfaces (there are four lens surfaces in the illustrated double lens goggle 10) is chosen such as to minimize one or more of power, prism and astigmatism to produce an optically correct lens in the mounted and as-worn orientation.

In accordance with the preferred embodiment, the double lens goggle 10 is optically correct in the as-worn orientation. "Optically correct," as that term is used in the present description, refers to a lens which demonstrates relatively low distortion in the preselected (e.g. straight ahead) line of sight as measured by one or more of the following values: prismatic distortion, refractive power and astigmatism. Raked lenses in accordance with the preferred embodiment demonstrate less than about ⅛ diopter prismatic distortion, preferably less than about 1/16 diopter, and more preferably less than about 1/32 diopter. Refractive power and astigmatism for lenses in accordance with the present invention are also preferably low. Each of refractive power and astigmatism are preferably less than about ⅛ diopter, more preferably less than about 1/16 diopter and most preferably less than about 1/32 diopter.

Optical correction is provided to the goggle 10, at least in part, through appropriate selection of lens thicknesses for each of the outer lens 12 and the inner lens 14. In particular, the thickness of one or both of the lenses 12, 14 are tapered, in one or more of the horizontal and vertical dimensions, to minimize prismatic distortion, refractive power and/or astigmatism.

Tapered Lenses In General

Figure 11:
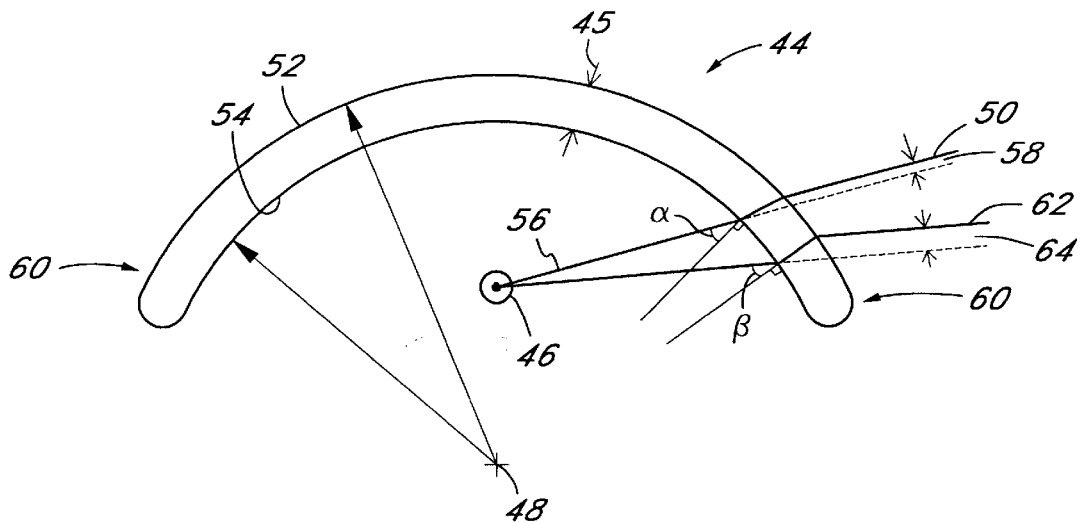
FIG. 11 is a schematic horizontal cross-sectional view of a prior art untapered lens for dual lens eyeglasses.
Figure 12:
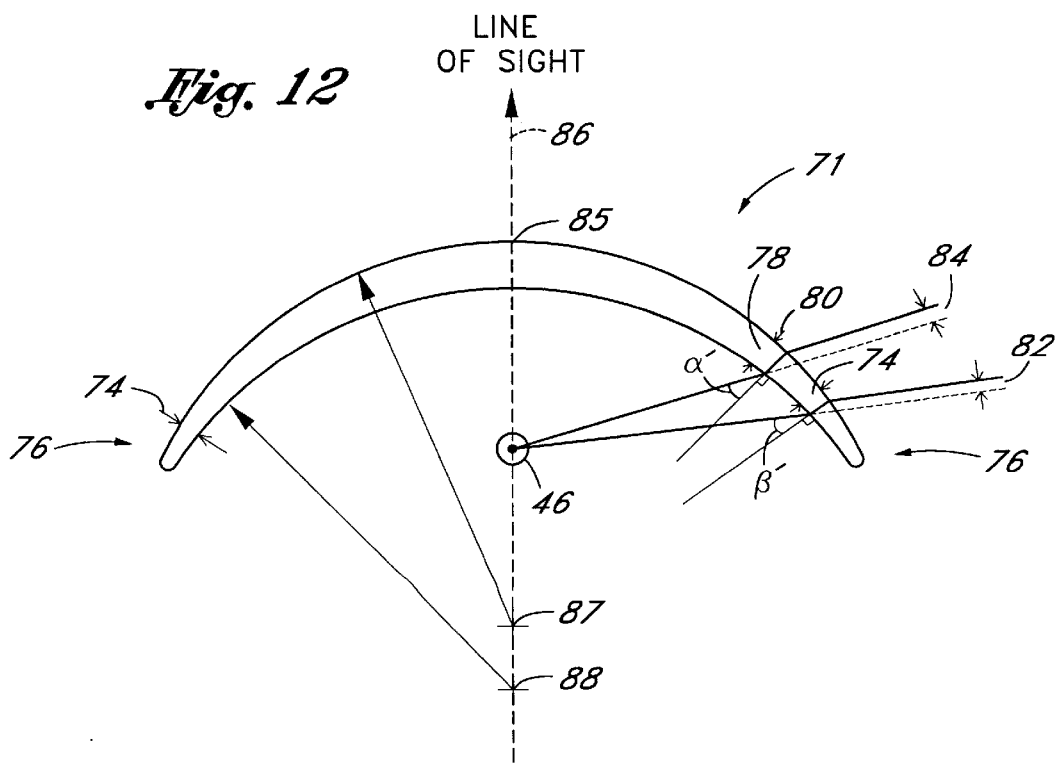
FIG. 12 is a schematic horizontal cross-sectional view of a tapered lens for dual lens eyeglasses.

FIGS. 11 and 12 illustrate, in the context of a centrally oriented lens in a dual lens eyeglass, the general concept of tapering to reduce prismatic distortion. FIG. 11 schematically illustrates refraction in a prior art lens 44 with circular inside and outside surface horizontal cross-sections, having a uniform thickness 45. With such a lens 44, the angle of incidence of rays from the lens 44 to the eye 46 changes throughout the angular range of vision. For example, a ray which shall be referred to for descriptive purposes as a medial light ray 50 strikes the lens 44 at an angle a to the normal at the point of incidence. As is well known in this art, bending of light at transmitting surfaces depends in part upon the angle of incidence of light rays. The ray 50 is refracted or bent in opposite directions at each of an outer surface 52 and an inner surface 54 of the lens 44, resulting in a transmitted ray 56 parallel to the incident ray 50. The transmitted ray 50 is laterally displaced, relative to the path of the incident ray 50, by a distance 58. This displacement represents a first order source of (prismatic) optical distortion.

Furthermore, refractory displacement is even more pronounced at a lateral end 60 due to a greater angle of incidence β. A peripheral incident ray 62 experiences greater displacement 64 than the medial incident ray 50, in accordance with Snell's Law, as will be understood by those of ordinary skill in the optical arts. The discrepancy between the peripheral ray displacement 64 and the medial ray displacement 58 results in a second order of optical distortion. This second order of distortion may cause substantial warping of an image seen through relatively lateral portions of the lens 44.

FIG. 12 schematically illustrates a lens 71 of tapered thickness, to compensate for the greater angle of incidence at the lateral ends 60 of the lens 44 (FIG. 11), similar in ways to that disclosed in the context of unitary lens sunglasses in U.S. Pat. No. 4,859,048, issued to Jannard. Tapering produces a smaller lens thickness 74 at a lateral end 76, relative to a lens thickness 78 at a more medial point 80. This smaller thickness 74 reduces an amount of peripheral ray displacement 82, relative to the peripheral ray displacement 64 through the untapered lens 44 of FIG. 12. In other words, lesser lens thickness 74 near the lateral end 76 of the tapered lens 71 compensates to some extent for a greater angle of incidence β', relative to the thickness 78 and angle of incidence α' at the more medial point 80.

The resulting difference between peripheral ray displacement 82 and medial ray displacement 84 on the same lens 71 is not as great as the corresponding difference in FIG. 11, reducing the second order optical distortion. Note that the degree of correction of the second order distortion depends upon a relationship between the manner and degree of tapering from the apex 85 to each lateral end 76 and the manner in which the angle of incidence changes over the same range.

The lens 71 of FIG. 12 is illustrated as though it were mounted within a frame (not shown) such that the wearer's normal line of sight 86 passes perpendicularly through the lens 71 at the lens apex or mechanical center 85. In other words, the angle of incidence to the lens normal is zero for the wearer's normal line of sight. The outer and inner surfaces of lens 71 in the cross-sectional illustration conform to offset, equal-radius circles represented by centerpoints 87 and 88, respectively. A line drawn through centerpoints 87 and 88, referred to herein as the optical centerline of the lens, is collinear with the normal line of sight in the as-worn orientation. This conventional configuration shall be defined as a centrally oriented lens, for ease of description. Circumferentially clockwise or counterclockwise of the normal line of sight 86, the angle of incidence to the lens normal increases in a regular fashion from zero at the lens apex 85.

While untapered, centrally-oriented dual lens eyewear exhibits a high degree of optical distortion, as set forth in FIG. 11, such distortion is exacerbated for unitary lens eyewear, and particularly for unitary lenses exhibiting high degrees of wrap and rake in the as-worn orientation, as those terms are defined below.

Preferred Embodiments

In accordance with the preferred embodiments, the front and rear surfaces of each lens in the double lens goggle 10 are configured to optically correct the goggle 10 in the as-worn orientation, as those terms are used above, by any of a number of manners. Most generally, a method of designing an optically correct double lens goggle includes selecting a first lens, selecting an interlens spacing, and selecting a second lens to produce an optically correct system. For example, one of skill in the art will recognize, in light of the present disclosure, that two concentric (uniformly thick) lenses can be spaced with selected base curves to optically correct the goggle. Numerous ray tracing software programs, such as Opticad™, are available to calculate the lens curvatures, thicknesses, and spacings as taught herein.

Figure 13:
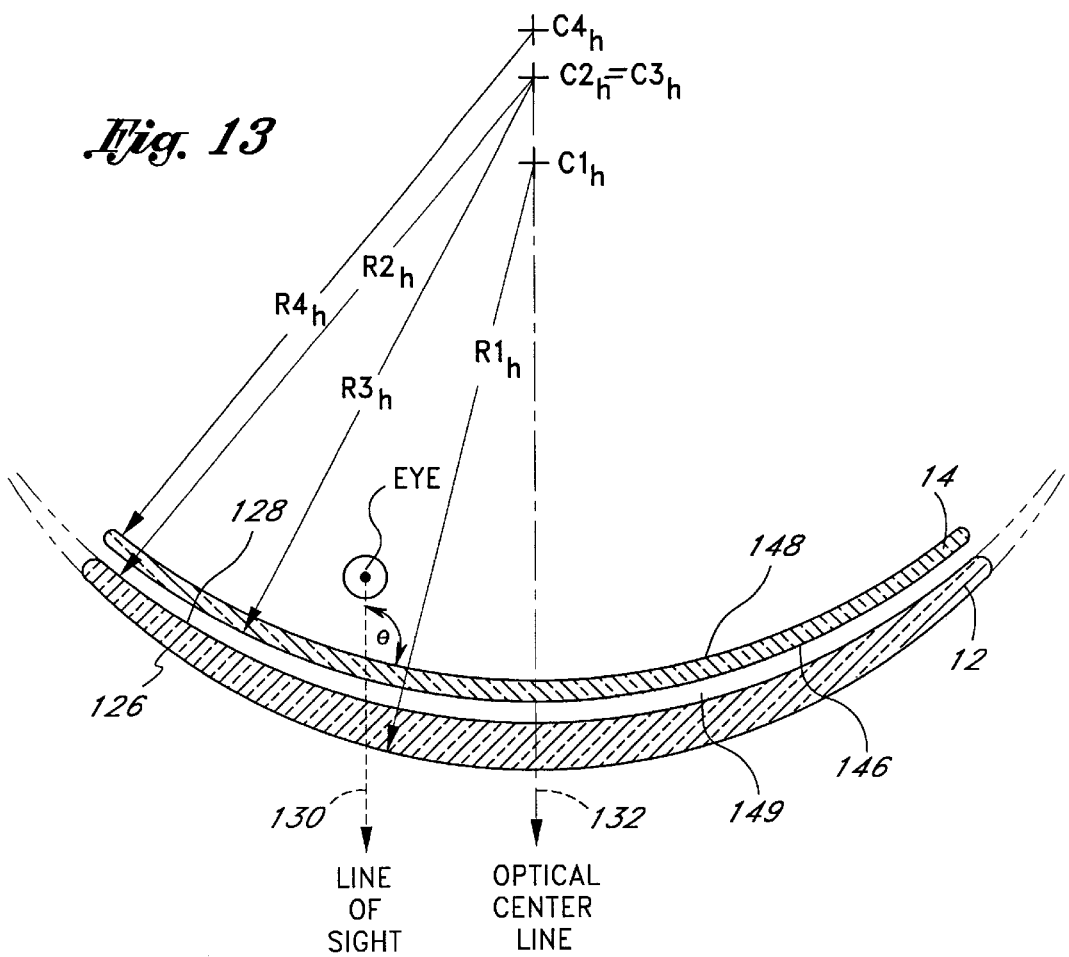
FIG. 13 is a schematic horizontal cross-section of a double lens system of FIG. 9 without the frame, constructed and oriented in the horizontal dimension in accordance with a preferred embodiment of the present invention.

As shown in FIGS. 13, however, preferably at least one of the unitary lenses 12, 14 of the illustrated double lens goggle 10 is tapered. As is known in the optical arts, a desirably smooth, regularly tapered thickness can be provided by having front and rear surfaces of the lens conform to shapes of different curvatures and/or offset centers of curvature. One of skill in the art will understand that centers of curvature may take different forms, and can be related to focal points, for example, for elliptical curvatures. Commonly, each lens surface will conform to a circular curvature in a given dimension (e.g., horizontal or vertical). A tapered lens can thus be provided with front and rear surfaces conforming to circles of different radius and/or offset centers.

As previously noted, each surface of the preferred lenses is toroidal. Accordingly, the radii and offset centers can be different in a vertical plane than they are in a horizontal plane. In other words, vertical tapering can be provided independently of horizontal tapering.

Exemplary Outer Lens

As shown in FIG. 13 with regard to the horizontal dimension, the curvature of a front surface 126 of the outer lens 12 of the preferred embodiment conforms to a circle of radius $R1_h$ in a given horizontal plane, with the circle centered upon the point $C1_h$. The curvature of a rear surface 128 of the lens 12 conforms to a circle of radius $R2_h$ in the horizontal plane, with the circle centered upon the point $C2_h$, where $C1_h$ and $C2_h$ are offset from one another. In the illustrated embodiment, the thickness of the outer lens 12 tapers from a central maximum thickness at the point where an optical axis or centerline 132 crosses the lens.

Preferably, the radii $R1_h$ and $R2_h$ and the offset between centers $C1_h$ and $C2_h$ are selected to provide lateral edge thicknesses from about 1% to about 99% of the thickness at the centerline 132, preferably from about 40% to about 90%, and most preferably about 72%. It will be understood that the arc length of the lens, along with the rate of taper, dictate the lateral edge thickness.

Preferably, the thickness of the lens 12 tapers smoothly, though not necessarily linearly, from the maximum thickness at the centerline 132 to a relatively lesser thickness at the lateral edge. The centerline thickness, also determined by the radii and offset, can be selected for the particular application, but is preferably between about 0.040 inch and 0.090 inch, more preferably between about 0.055 inch and 0.080 inch, and is about 0.069 inch for a particular ski goggle application The minimum thickness at lateral edge is generally governed by the desired impact resistance (particularly for the outer lens 12) of the lens. For ski goggle applications, the thicknesses provide a balance between the structural needs for impact resistance and the need for light weight and flexibility for the preferred materials.

FIG. 15 schematically illustrates tapering of the outer lens 12 in a vertical plane. The skilled artisan will recognize that a construction of a vertically tapered thickness can be made independently of the horizontally tapered thickness for the preferred toroidal embodiments. The centers of curvature for the horizontal and vertical planes will generally not be coincident for a toroidal surface. Preferably, however, the centers are aligned on a common optical centerline 132.

An exemplary outer lens 12 for use in the double lens goggle 10 includes the following horizontal dimensions: $R1_h$=3.2624 inches; $R2_h$=3.2256 inches; the center thickness is about 0.069 inch; $C1_h$ and $C2_h$ are offset by about 0.032 inch; and the horizontal arc length is about 7.0 inches, subtended by an angle of about 120°–125°. The same outer lens 12 includes the following vertical dimensions: $R1_v$=5.046 inches; $R2_v$=4.9763 inches; $C1_v$ and $C2_v$ are offset by about 0.001 inch; and the vertical arc length ranges from about 2.0 inches at the medial nose recess to about 2.7 inches in front of each eye.

First Exemplary Inner Lens

Referring still to FIGS. 13 and 15, having constructed a first tapered lens (the outer lens 12 of the illustrated embodiment), the second lens (the inner lens 14 of the illustrated embodiment) is constructed and spaced from the first lens in such a manner as to produce an optically correct double lens goggle 10. Accordingly, a front surface 146, a rear surface 148, and an interlens spacing 149 is selected. Preferably, regardless of the rear surface 148 of the inner lens 14, the front surface 146 of the inner lens 14 is selected to be concentric with the rear surface 128 of the outer lens 12. In this way, an interlens spacing 149 is constant over the entire double lens system, and the gasket 15 separating the lenses 12, 14 can be provided in a uniform thickness without being subject to excessive shearing forces as the double lens goggle 10 is flexed. Furthermore, a constant interlens spacing 149 generally facilitates consistent insulating properties over the entire viewing window 18, such that fogging does not preferentially occur in particular spots.

In accordance with a concentric embodiment, the inner lens 14 is provided with front and rear surfaces 146, 148 which are concentric, i.e., defining a uniform thickness, in each of the vertical and horizontal dimensions. Specifically, the inner lens 14 preferably has a substantially constant thickness between about 0.020 inch and about 0.040 inch, more preferably between about 0.025 inch and 0.035 inch, and most preferably about 0.030 inch. A goggle incorporating this concentric inner lens 14 and the exemplary outer lens 12, described above, can have a preferred interlens spacing 149 between about 0.030 inch and 0.090 inch, and more preferably about 0.0625 inch As the inner lens 14 generally need not withstand impact in use, and need only define the insulating space 149, it can be made thin, as described, such as to reduce optical disturbance.

As the surfaces are concentric, the radius of front curvature $R3_h$ of the inner lens 14 can be calculated by subtracting the interlens spacing from the radius of rear curvature $R2_h$ of the outer lens 12, and similarly in the vertical dimension. The radii of rear curvature $R4_h$ and $R4_v$ can similarly be calculated from the front curvatures by subtracting the inner lens thickness, as will be understood by one of skill in the art Though not illustrated as such in FIGS. 13 and 15, for this concentric embodiment, the centers of curvature C2, C3 and C4 are all coincident in each of the vertical and horizontal dimensions, though the vertical centers $C2_v=C3_v=C4_v$ are not generally coincident with horizontal centers for the illustrated non-spherical, toroidal embodiment.

The goggle 10 having the concentric inner lens 14 exhibited sphere or refractive power of about −0.02 diopter, cylinder power (astigmatism) of about −0.03 diopter, and no measurable or appreciable prism along the optical axis. Measured along the normal lines of sight in an as-worn orientation, assuming an interpupillary distance (ILD) of 64 mm, the goggle 10 having the concentric inner lens 14 exhibited sphere or refractive power of about −0.03 diopter, cylinder power (astigmatism) of about −0.06 diopter, and about 0.20 Δ base out prism. The lenses 12, 14 are centrally oriented in the as-worn orientation for these measurements, though not illustrated as such in FIG. 15.

By way of contrast, the exemplary outer lens 12 mounted without an inner lens (i.e., in a conventional goggle with a single unitary lens) exhibited refractive power of about +0.01 diopter, astigmatism of about −0.01 diopter, and about 0.02 Δ base in prism along the normal lines of sight. Accordingly, the uniformly thick inner lens 14, while optically correct in terms of refractive power and astigmatism, introduces greater power, astigmatism and prism relative to a goggle without an inner lens. A goggle 10 constructed in accordance with the first embodiment nevertheless demonstrates improved optics relative to a conventional double lens system incorporating two spaced, uniformly thick lenses.

Second Exemplary Inner Lens

In accordance with a second embodiment, the second lens (inner lens 14 in the given example) is selected to compensate for distortion introduced by the first lens (outer lens 12 in the given example). It will be understood that the term "compensate," as used herein, does not refer to a reduction of optical distortion relative to the first lens alone. Rather, the second lens will in general "compensate" for the first lens when the selection of the second lens and the interlens spacing takes into consideration the optical effect of the first lens. Such compensation manifests itself in a double lens system in levels of distortion which are improved relative to a double lens system with the same first lens but wherein the second lens is concentric and uniformly spaced from the first lens (such as the first exemplary inner lens discussed above). More concretely, such compensation can be achieved through appropriate selection of the interlens spacing and/or second lens thickness, preferably with the aid of a ray tracing program.

Desirably, the interlens spacing is as described above. The inner lens 14 is thus preferably constructed with the front surface 146 concentric with the rear surface 128 of the exemplary outer lens 12, as described above, to facilitate use of the constant thickness gasket 16. Thus, in the illustrated embodiment, compensation is achieved through selection of the rear surface 148 of the inner lens 14 to establish a second lens thickness.

In the illustrated embodiment, the radii of rear curvature $R4_h$ and $R4_v$ are 3.1359 inches and 4.8606 inches, respectively. The selected dimensions result in positive power in the horizontal dimension, and negative power in the vertical dimension, for the inner lens 14 alone. The center of curvature $C4_h$ in the horizontal dimension is offset behind $C3_h$ by about 0.0078 inch (FIG. 13), while the center of curvature $C4_v$ in the vertical dimension is offset forward of $C3_v$ by about 0.0182 inch (FIG. 15).

Given the preferred arc length of the lens 14 and assuming a central orientation, the thickness of the inner lens 14 thus tapers in the horizontal dimension from a central maximal thickness of about 0.035 inch to a lateral edge thickness at either lateral end of about 0.030 inch. In the vertical dimension, the lens 14 tapers from a central minimal thickness of about 0.035 inch to top and bottom edge thicknesses of about 0.036 inch.

Optical distortion of the resultant goggle 10, including both the exemplary toroidal, tapered outer lens 12 and the toroidal, tapered inner lens 14, is further reduced, relative to the first embodiment which has a uniformly thick inner lens. Measured along the normal lines of sight in an as-worn orientation, assuming a pupillary distance of 64 mm, the goggle 10 having the tapered inner lens 14 exhibited sphere or refractive power of about −0.04 diopter, no measurable or appreciable cylinder power (astigmatism), and about 0.12 Δ base out prism. As with the previous embodiment, the lenses 12, 14 are centrally oriented in the as-worn orientation for purposes of construction and measurement, although not illustrated as such in FIG. 15.

Figure 10A:
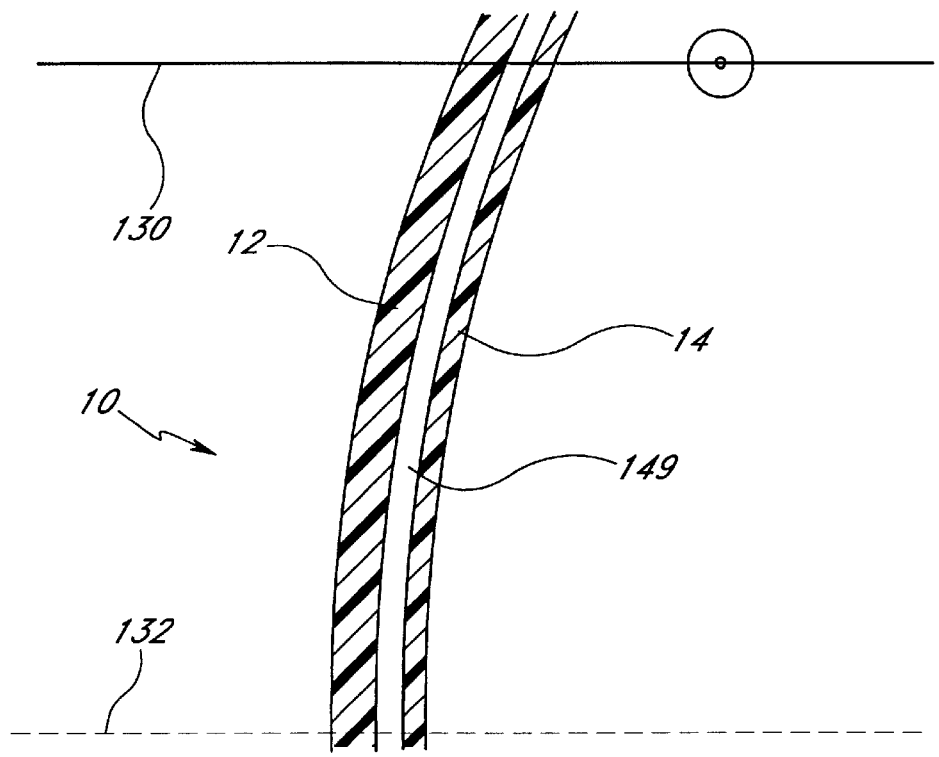
FIGS. 10A and 10B are schematic ray trace diagrams in accordance with a preferred double lens eyewear system.
Figure 10B:
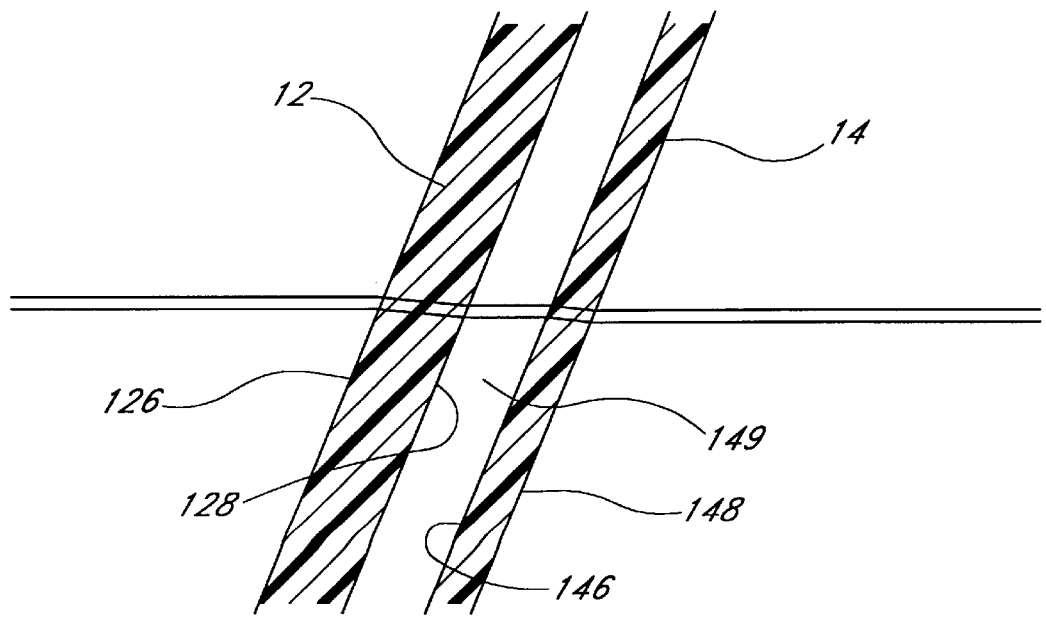

FIG. 10A graphically illustrates the optical quality of the preferred double lens goggle 10 of the second embodiment, wherein each of the outer lens 12 and inner lens 14 is tapered. A pair of rays are illustrated passing through the goggle lenses 12, 14 along the wearer's normal line of sight 130, parallel to the optical centerline 132 of the lens system. FIG. 10B is a magnified image of the rays, schematically showing refraction of the parallel rays at the front and rear surfaces 126, 128 of the outer lens 12, and then through the rear and front surfaces 146, 148 of the inner lens 14.

The low power of the second preferred embodiment is illustrated by the fact that the pair of rays remain substantially parallel to one another after passing through both lenses 12, 14. Accordingly, the rays do not appreciably converge or diverge.

Moreover, the drawings also show the low level of prism produced by the goggle 10 incorporating these lenses 12, 14. The ray paths on the viewer side of the goggle 10 remain substantially parallel to the incident path, and only slightly displaced. Although the rays deviate somewhat from the incident direction after passing through the outer lens 12, the inner lens 14 returns the rays to a path substantially parallel with the incident path, with little lateral displacement of the rays.

It will be understood by the skilled artisan that the advantages in minimizing optical distortion apply to both the horizontal and the vertical dimensions. Particular advantage is derived by applying the principles taught herein to both vertical and horizontal dimensions of the lens, enabling the combination of lateral and lower peripheral protection of the eyes (through wrap and rake) with excellent optical quality over the wearer's full angular range of vision.

Oriented and Optically Correct Lenses For Rake and/or Wrap

The lenses 12, 14 as described above reduce optical distortion in a goggle application, and particularly in the double lens goggle 10. The present invention further provides optically corrected goggles in non-conventionally oriented lenses. As described in U.S. Pat. No. 5,648,832, the disclosure of which is hereby incorporated by reference, non-prescription eyewear having lenses mounted with a high degree of rake and/or wrap in the as-worn orientation have tended to exhibit optical distortion. Such rake and wrap are particularly useful in goggle applications.

Desirable Ski Goggle Orientations

A degree of wrap may be desirable for aesthetic styling reasons, for lateral protection of the eyes from flying debris, snow or ice, or for interception of peripheral light. In the ski goggle application, such wrap additionally aids in defining an enclosed space by approaching the wearer's temples. Wrap may be attained by utilizing lenses of tight horizontal curvature (high base), such as the preferred small-radius toroidal lenses 12 and/or 14. As a result, prior art goggles with substantial "wrap" around the sides of a wearer's face has generally been accompanied by some degree of prismatic distortion.

Figure 14:
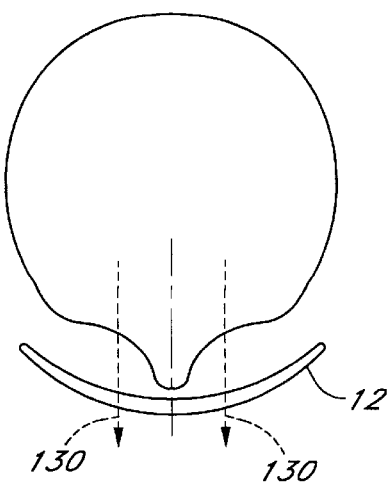
FIG. 14 is a schematic top plan view of a unitary lens having a high wrap in relation to a wearer.

FIG. 14 schematically illustrates the horizontal cross-section of a unitary ski goggle lens 12 in relation to the wearer's head, and more particularly to the wearer's lines of sight 130. When the goggle is worn, a lateral edge of the lens wraps significantly around and comes in close proximity to the wearer's temple to provide significant lateral eye protection.

As is apparent from the schematic view of FIG. 13, the wearer's normal line of sight 130 in the horizontal dimension no longer crosses the lens 12 and/or 14 perpendicularly, as a consequence of the increased wrap. Instead, the angle of incidence θ for the wearer's line of sight 130 is generally greater than 90°, and to achieve good wrap it may be greater than about 95°, preferably is within the range of from about 100° to about 135°, and in one unitary lens embodiment with a radius of horizontal curvature of about 3.2 inches, θ is about 112.716°.

Similarly, a high degree of rake or vertical tilting may be desirable for aesthetic reasons and for intercepting light, wind, dust or other debris from above or below the wearer's eyes. Prior art dual lens eyewear with substantial rake generally also display a degree of prismatic distortion.

In general, "rake" will be understood to describe the condition of a lens, in the as-worn orientation, for which the normal line of sight 130 in the vertical dimension (see FIG. 15) strikes a tangent at the surface of the lens 120 at a non-perpendicular angle, as described with respect to lenses with high wrap. It is often advantageous in goggle applications, and particularly in snow skiing applications, to have downward rake, to protect the face from snow and ice, and also to intercept light from the direction the skier is often looking, i.e., below. Thus, to achieve useful rake in a skiing application, the normal line of sight 130 in the vertical dimension passes through lens surfaces with an angle of incidence of greater than about 92–93°, more preferably between about 95° and 135° for good protection. The angle of incidence for a particular raked lens for a ski goggle application is about 97°. For some designs the angle will be at least about 98° or 100°, and other designs have an angle within the range of from about 100° to about 118°.

Optically Correct Goggles with Rake and/or Wrap

In accordance with the preferred embodiment, optical correction can be obtained even for goggles with one or more lenses mounted with a high degree of rake and/or wrap. In general, the form of the taper is related to the wearer's normal line of sight in the as-worn orientation. For this purpose, an optical centerline defines a directionality to the tapered lens, as briefly noted above. Generally, the optical centerline represents an axis of rotational symmetry for a tapered lens. The optical centerline may thus often pass through the thinnest or thickest point on a tapered lens.

Conventionally, for a spherical tapered lens, the optical centerline is that line which passes through both center points of the offset spheres to which the front and rear surfaces conform. This happens to pass through the thickest portion of the tapered geometrical shape to which the lens surfaces conform, though the centerline need not necessarily pass through the lens itself. See, for example, FIGS. 6, 7 and 12 of U.S. Pat. No. 5,648,832, showing a lens and lens blank for dual lens eyewear in relation to an optical centerline 132 and the optical center at which it passes through a lens blank.

In the illustrated embodiments of the present invention, the surfaces 126, 128, 146, 148 of the toroidal lenses 12, 14 do not have coincident centers of horizontal and vertical curvature. Nevertheless, the lenses 12, 14 can be arranged such that each of the centers of curvature align with one another to define a unique optical centerline 132. In accordance with the preferred embodiments, the lenses 12, 14 are so arranged, such that the double lens goggle 10 has a unique optical centerline, as illustrated in FIGS. 13 and 15. It will be understood by one of ordinary skill in the art, in light of the disclosure herein, that in other arrangements, the lenses 12, 14 can define multiple optical centerlines which are parallel to one another.

Referring to FIGS. 13 and 15, at least one lens is provided for a goggle, the optical centerline 132 of which is preferably aligned with rake to be substantially parallel with the wearer's normal lines of sight 130 in the as-worn orientation. More preferably, the goggle includes outer and inner lenses 12, 14, as shown, and more preferably both of the lenses 12, 14 are raked and have a common optical centerline 132 aligned to be substantially parallel with the wearer's normal lines of sight 130 in the as-worn orientation. Desirably, the substantially parallel relationship is maintained in either of the horizontal dimension (see FIG. 13) or the vertical dimension (see FIG. 15), but most preferably the optical centerline 132 is substantially parallel with the wearer's normal lines of sight 130 in each of the horizontal and vertical dimensions.

For purposes of the present invention, "substantially parallel" shall mean that the preselected line of sight 130 when the lens 120 is oriented in the as worn position generally does not deviate within the horizontal or vertical plane by more than about ±12° from parallel to the optical centerline 132. Preferably, the normal line of sight 130 should not deviate by more than about ±10° from the optical centerline 132, more preferably the normal line of sight 130 deviates by no more than about ±8° and most preferably no more than about ±5° from parallel to the optical centerline 132. Optimally, the line of sight 130 is parallel to the optical centerline in the as worn orientation.

Variations from parallel in the horizontal plane generally have a greater negative impact on the optics than variations from parallel in the vertical plane. Accordingly, the solid angle between the line of sight 130 and optical centerline 132 in the vertical plane may exceed the ranges set forth above, for some eyewear, as long as the horizontal component of the angle of deviation is within the above-mentioned ranges of deviation from the parallel orientation. Preferably, however, the line of sight 130 deviates in the vertical plane in the as-worn orientation within the ranges set forth above.

As shown in FIG. 13, at least one of and preferably both of the lenses 12, 14 are centrally oriented (i.e., symmetrically with respect to the wearer's face) in the horizontal dimension in the as-worn orientation. Accordingly, the optical centerline 132 will generally be substantially parallel with the wearer's normal lines of sight 130, as shown with regard to one of the wearer's eyes.

FIG. 15 illustrates a vertical cross-section of the lenses 12, 14. As with the horizontal dimension, as least one of and preferably both lenses 12, 14 are configured such that their optical centerline 132 (common to both lenses in the illustrated embodiment) is substantially parallel to the wearer's normal lines of sight 130 in the as-worn orientation. Unlike the horizontal dimension, however, the lenses are not centrally oriented in vertical dimension due to a degree of rake which is desirable in the ski goggle application.

For optically corrected eyewear in accordance with the preferred embodiment, however, the normal line of sight 130 to a raked lens 12 or 14 is most preferably parallel to and vertically offset or displaced from the optical centerline 132, as shown in FIGS. 15 and 15A. Therefore, the degree of rake in a correctly oriented lens may be measured by the distance which the normal line of sight is vertically displaced up or down from the optical centerline.

For a centrally oriented lens, as shown in FIG. 15B, the wearer's line of sight to be coincides with both the optical centerline and the mechanical centerline, thus displaying no vertical displacement. FIG. 15C shows a lens orientation which is downwardly tilted or raked, but for which the optical centerline and the normal line of sight are highly divergent such that no "displacement" could meaningfully be measured. While such a lens may have downward rake in a conventional sense, advantageously providing downward protection for the eye and conforming to the wearer's face, it is not optically corrected in the as-worn orientation for the straight ahead line of sight.

In contrast, the normal line of sight through a raked lens, made in accordance with the preferred embodiment, is characterized by a finite vertical displacement from the optical centerline, preferably a downward displacement for downward rake. Where the optical centerline diverges from the normal line of sight within the acceptable angular ranges set forth above, this displacement should be measured at or near the lens surface. The displacement may range from about any non-zero displacement to about 8.0 inches. Lenses of lower base curvature may require a greater displacement in order to achieve good rake. The vertical displacement for a lens of base 6 curvature, however, should be between about 0.1 inch and about 2.0 inches. More preferably, the vertical displacement is between about 0.1 inch and about 1.0 inch, particularly between about 0.25 inch and about 0.75 inch, and most preferably about 0.5 inch.

Viewed from a different perspective, the lens(es) of the preferred embodiments can be characterized by an optical centerline as has been disclosed previously herein, and a mechanical centerline. The mechanical centerline is a line that extends through the lens at a point lying halfway between the left side and the right side of the lens and also halfway between the top edge and the bottom edge of the lens. The mechanical centerline extends through the lens at that point at a perpendicular to a tangent to the surface of the lens at that point. Application of the present invention in terms of the mechanical centerline is illustrated with respect to upwardly raked goggles in FIGS. 15D and 15E. It will be understood by one of skill in the art, however, that this perspective may also be applied to the downwardly raked embodiments discussed above.

Figure 15E:
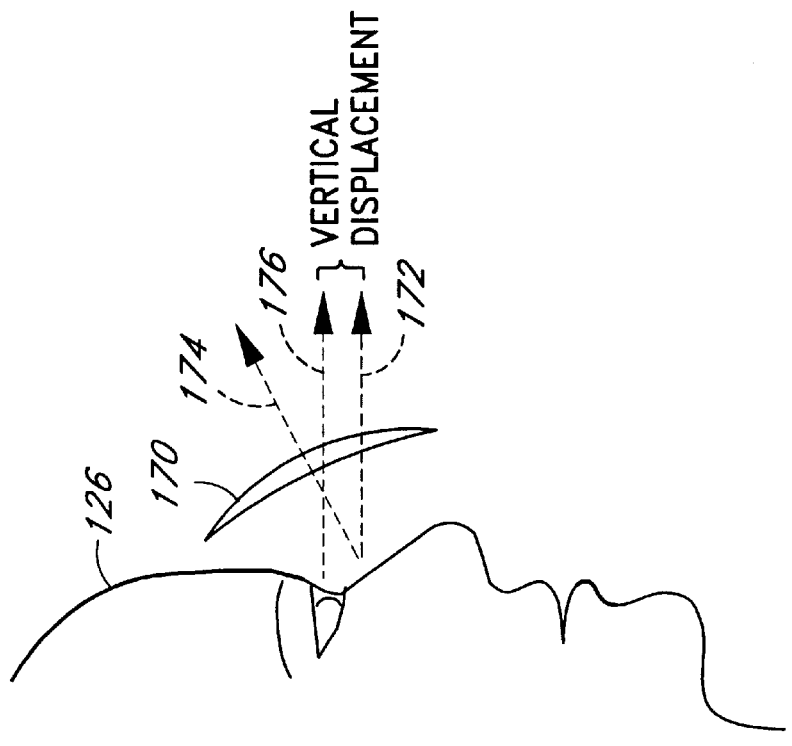
Figure 15D:
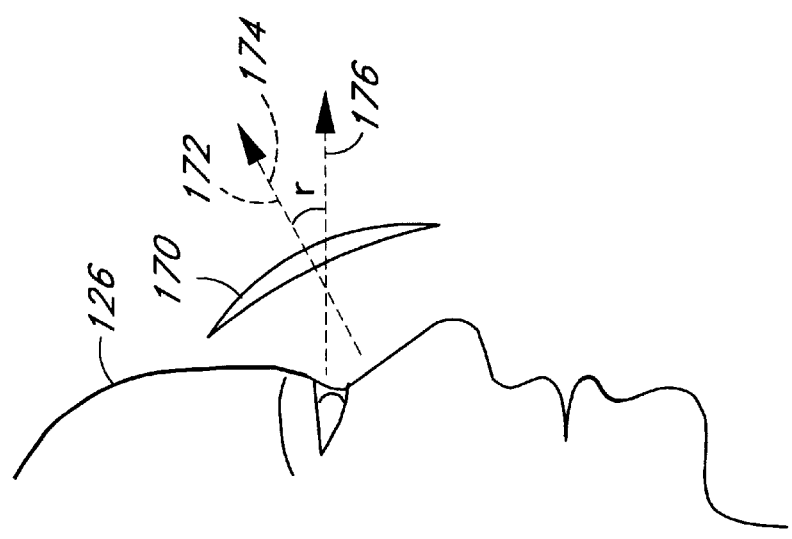

FIG. 15D illustrates a tapered unitary lens 170 which has upward rake, as may be desired for many goggle applications. However, the illustrated lens 170 is mounted in such a manner that an optical centerline 172 of the lens 170 is coincident with the mechanical centerline 174 of the lens 170. The mechanical centerline 174 is not, however, coincident with a wearer's straight-ahead normal line of sight 176. Rather, the mechanical centerline 174 of the lens 170 is angled upwardly in a forward direction from the wearer with respect to the wearer's straight-ahead normal line of sight 176 by an angle r. As a consequence, in accordance with the principles previously disclosed herein, at least prismatic distortion is introduced with respect to the wearer's straight-ahead normal line of sight 176.

Referring to FIG. 15E, however, lenses or shields produced in accordance with the present invention, on the other hand, are provided with an angular deviation between the optical centerline 172 and the mechanical centerline 174 in the vertical plane, while the optical centerline 172 is substantially parallel with the normal line of sight 176. The degree of angular deviation between the optical centerline and the mechanical centerline in the vertical plane will depend upon the degree of rake with which the lens is ultimately mounted in the as-worn orientation to achieve optical correction. Generally the angle will be more than about 2° or 3°, and typically will be within the range of from about 5° to about 45°. For some designs the angle will be at least about 8° or 10°, and other designs have an angle within the range of from about 10° to about 18°. This lens geometry permits the lens to be mounted such that the mechanical centerline extends at an angle with respect to the wearer's straight-ahead normal line of sight in the as-worn orientation but the optical centerline remains substantially parallel to the wearer's straight-ahead normal line of sight in the as-worn orientation.

Thus, in accordance with the present invention, the lens 170 is cut from a blank or molded such that, in the vertical plane, the optical centerline 172 is rotated away from the mechanical centerline 174. For a lens which is to be mounted with upward rake, the optical centerline will also be displaced downwardly from the normal line of sight 176. Refer for comparison to FIGS. 15, 15A, and 17 which illustrate correction in the vertical plane for an eyeglass having downward rake.

Once the lens is properly configured (e.g., by molding or cutting as set forth below), it is then oriented in the support structure such that it retains a parallel or substantially parallel relationship between the wearer's preselected reference line of sight and the optical centerline 172 of the lens. For most applications, the wearer's preselected reference line of sight will be the wearer's straight-ahead normal line of sight 176. Thus, referring to the vertical plane orientation illustrated in FIG. 15E, the goggle lens 170 of the present invention is configured such that the optical centerline 172 of the lens 170 is spaced apart from but substantially parallel to the wearer's straight-ahead normal line of sight 176 in the as-worn orientation. The ideal orientation of the lens in a goggle frame also maintains the horizontal view optical centerline of the lens (not illustrated) substantially parallel to the wearer's straight-ahead normal line of sight. As with previous embodiments, the properly tapered and oriented lens will be optically corrected if at least one and preferably two or all three of prism, power and astigmatism are less than about ⅛ diopter, more preferably less than about ¹⁄₁₆ diopter and optimally less than about ¹⁄₃₂ diopter.

A lens having the geometry described above can then be oriented and mounted in the support structure (such as the illustrated goggle frame 16) in any of a wide variety of manners well understood for each respective type of support structure. For example, lenses for use in ski goggles or swim masks may be fit within gaskets inside annular recesses provided for that purpose, as well as other retention systems which will be well understood by those of skill in the art.

Method of Manufacturing Oriented Lenses

The lenses 12, 14 in accordance with the present invention can be manufactured by any of a variety of processes well known in the art. Typically, high optical quality lenses are cut from a preformed injection molded lens blank Alternatively, the lens can be molded directly into its final shape and size, to eliminate the need for post-molding cutting steps.

Preferably, the lens, or the lens blank from which it is cut, is injection molded and comprises an optically acceptable material, such as polycarbonate, CR-39, or any of a variety of high index plastics known in the art. Cellulosic materials, such as cellulose acetate butyrate and cellulose acetate proprionate, are also suitable for the preferred ski goggle application. The optical correction of the present invention may also be applicable to glass lenses, although the need for correction in the present context is generally more pronounced in currently popular nonglass materials. Furthermore, flexible polymeric materials are particularly advantageous for the illustrated ski goggle embodiment, as they can elastically deform with the flexible frame 16 to facilitate pulling the goggles 10 over the wearer's head.

If the lens is to be cut from a lens blank, the taper and curvature of a carefully preselected portion of the lens blank is transferred to the lens in accordance with a preferred orientation process described below. Preferably, the frame is provided with a slot or other attachment structure that cooperates with the molded curvature of the lens to minimize deviation from and even improve retention of the as-molded curvature.

Alternatively, the lens or lens blank can be stamped or cut from generally planar tapered sheet stock and then bent into the curved configuration in accordance with the present invention. This curved configuration can then be maintained by the use of a relatively rigid, curved frame, or by heating the curved sheet to retain its curved configuration, as is well known in the thermoforming art.

Most preferably, the curvature the front and rear surfaces of each of the lenses 12, 14 are created in the lens blank molding and polishing processes, and the lens shape is cut from the blank in accordance with the invention as described below. While the description below is thus mostly given in the context of cutting lenses from lens blanks, it will be apparent to one of ordinary skilled in the art that similar processes can be used conceptually or in reality to form a mold for injection molding lenses with the appropriate tapering for a given orientation.

Figure 16:
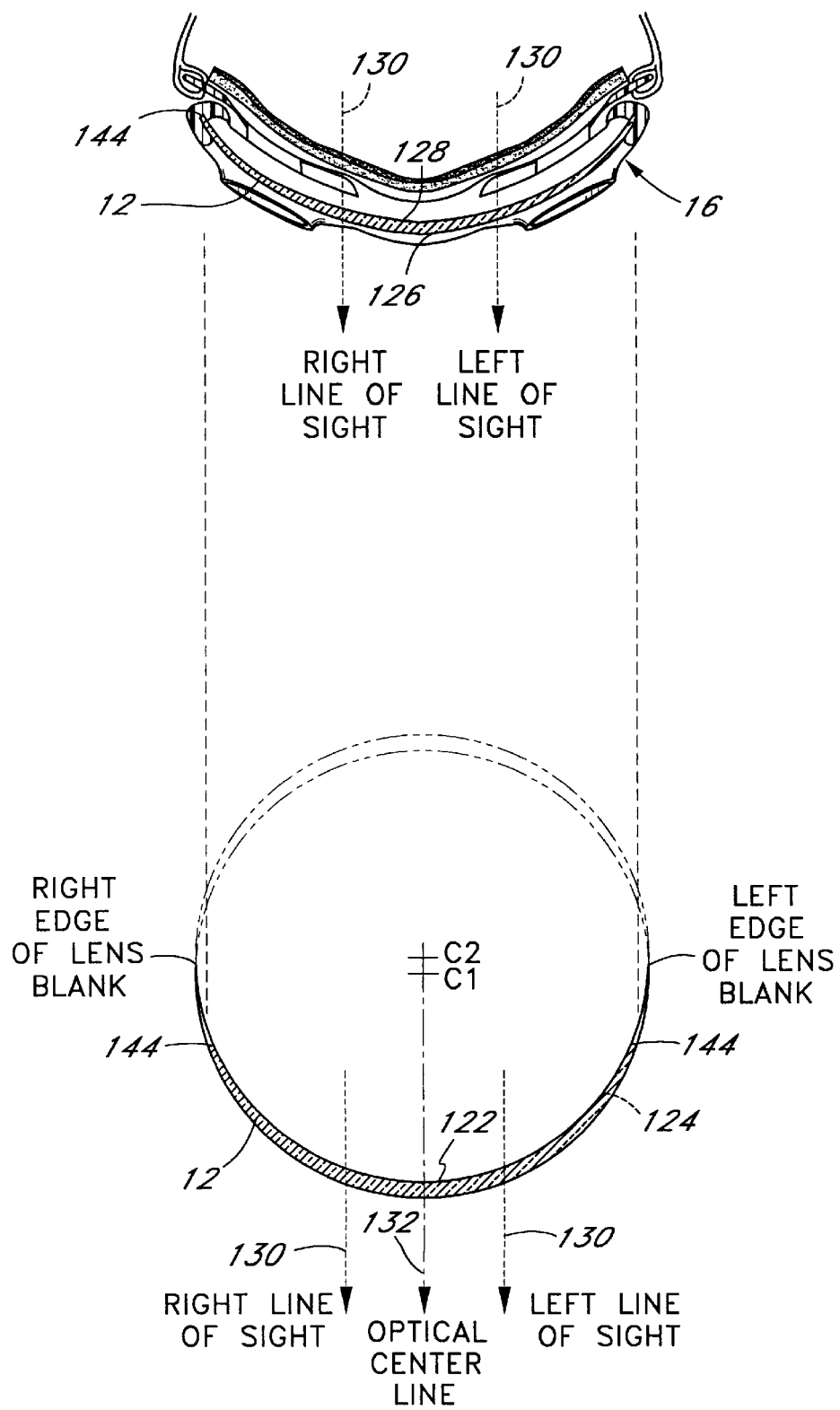
FIG. 16 schematically illustrates the projection of the lens horizontal profile from a desired orientation within a goggle frame to a lens blank, in accordance with a preferred embodiment of the present invention.

FIGS. 16 and 17 will aid in describing a method of choosing a location on a lens blank 140 from which to cut the outer lens 12, in accordance with a preferred embodiment of the present invention. It will be understood that a similar method can be used to construct the inner lens 14 for the double lens goggle of the preferred embodiment, and that one or both of the lenses 12, 14 can then be mounted with the orientations described above.

As a first step, a desired general curvature of the lens outer or inner surface 126, 128 may be chosen. As mentioned above, preferred orientations may provide significant lateral wrap for lateral protection and interception of peripheral light, and for aesthetic reasons. FIG. 14 illustrates more plainly how wrap may be related to the line of sight 130 of the wearer in the horizontal dimension. For the preferred lens 12, this choice determines the base value of the lens blank 140. As noted elsewhere herein, a number of other curvatures may be utilized in conjunction with the present invention. A choice of lens thickness may also be preselected. In particular, the minimum thickness may be selected such that the lens will withstand a preselected impact force.

A desired lens shape may also be chosen. For example, FIG. 2 illustrates an example of a front elevational shape for the lens 12. The particular shape chosen is generally not relevant to the oriented decentered lens optics disclosed herein.

A desired as-worn orientation for the lens should also be chosen, relative to the normal line of sight 130 of the wearer 126. As previously noted, the unitary lens 12 of the preferred ski goggle 10 will generally be centrally oriented in the horizontal dimension.

The eyewear designer may also choose a degree of rake, or vertical tilt, as will be understood from FIGS. 15A–15E, schematically illustrating various vertical as-worn orientations of a lens, relative to the head of the wearer. FIG. 15A illustrates a preferred downwardly raked orientation of the lens 12 relative to the head of the wearer, and relative in particular to the straight ahead normal line of sight 130. A downward rake, as illustrated in FIG. 15A, is desirable for certain eyeglass systems for a variety of reasons, including improved conformity to common head anatomy, and particularly for the downward viewing in the preferred ski goggle application. Some degree of upward rake may be desirable, for example, in certain goggle applications. See, e.g., FIG. 15E and accompanying text.

As will be apparent to those of skill in the art in view of the disclosure herein, a lens 12 having a mechanical center point which falls below the horizontal plane intersecting the optical centerline 132 will permit the lens to be oriented with a downward rake as illustrated in FIG. 17 and yet preserve a substantially parallel relationship between the optical centerline and the straight ahead line of sight to produce an optically correct lens in the properly as-worn orientation. Since the orientation of the lens 12 to the optical centerline 132 should be the same as the orientation between the lens 12 and a parallel to the normal line of sight 130 in the as-worn orientation, any lens cut from this sphere below the optical centerline 132 can be mounted with a corresponding degree of downward rake and achieve the optical correction of the present invention. Lenses centered above the optical centerline 132 can be optically corrected in an as-worn orientation with a commensurate degree of upward rake.

Accordingly, the desired degree of rake may be chosen by specifying a vertical component of the displacement between the normal line of sight 130 and the optical centerline 132, as illustrated in FIG. 15A. Either way, the greater the displacement, the greater the rake. In general, the vertical displacement in accordance with the present invention will be greater than zero. Generally, it will be from about 0.1 inches to about 2 inches in dual lens eyeglasses depending upon base curvature. Preferably, vertical displacement will be from about 0.1 inches to about one inch, or about 0.2 inches or greater. More preferably, it will be from about 0.25 inches to about 0.75 inches and in one embodiment it is about 0.5 inches.

Alternatively, a general profile may be chosen which fixes an orientation of the normal line of sight relative to the curvature of the lens (not accounting for the thickness of the lens). For instance, both FIGS. 15A and 17 provide reference points of a top edge 152 and a bottom edge 154 relative to the normal line of sight 130. This relationship may then be utilized to determine the position on a lens blank from which to cut the lens, as will be clear from the discussion of FIG. 17 below.

Referring now to FIG. 16, a mapping of the horizontal orientation of the lens 12 onto the lens blank 140 is illustrated. Each normal line of sight 130 is maintained substantially parallel to and offset from the optical centerline 132, in accordance with a horizontally centrally oriented embodiment.

Once the aesthetic design and desired rake and wrap orientation such as that illustrated in FIG. 16 has been determined (such as by the chosen frame 16), and the lens blank 140 formed having a suitable base curvature for fitting within the aesthetic design, the aesthetic design may be "projected" graphically or mathematically onto the surface of a theoretical three-dimensional shape (e.g., a sphere or toroid) or the blank 140 to reveal that portion of the blank which is suitable for use as the lens 12. The projection of the lens shape should be moved about the surface of the blank until it is positioned such that the lens cut from the blank at that location will exhibit the appropriate wrap and rake for the aesthetic design without any rotation of the lens 12 out of its orientation in which the optical centerline of the blank is substantially parallel to the desired normal line of sight in the as-worn orientation A similar projection may be performed for the chosen vertical orientation, as depicted in FIG. 17. FIG. 17 schematically represents the projection from the chosen frame 16 to a position on the lens blank 140. The frame 16 (or a conceptual configuration such as provided by Figure 15A) provides reference points in the form of the lens top edge 152 and bottom edge 154 in relation to the line of sight 130. The projection may then be shifted up or down until the top edge 152 and the bottom edge 154 are both simultaneously aligned with corresponding points on the outer surface of the lens blank, while maintaining the line of sight 130 substantially parallel with the optical centerline 132.

While conceptually separated in the above discussion, projection of both the horizontal profile and the vertical profile is preferably performed simultaneously, locating a unique position on the lens blank 140 corresponding to the desired three-dimensional shape of the lens (including the front elevational shape shown in FIG. 2) at which the line of sight 130 is parallel to the optical centerline 132 or other reference line of the lens blank 140. Of course, it will be understood that the lines 130 and 132 may be substantially parallel, that is, within the acceptable range of angular deviation set forth above.

This shape may then be cut from the blank 140 or molded directly in the final lens configuration. The resultant lens 12 not only conforms to the desired shape, but also minimizes prismatic distortion when in the as-worn orientation.

The shield 170 of the present invention which is corrected for upward rake must be conceptually cut from a position on the blank 140 which is shifted higher along the lens blank 140 compared to the lens 12 illustrated in FIG. 17.

Of course, this description is limited to a lens blank 140, which is described by an optical centerline passing through the central horizontal meridian (i.e., the lens blank 140 taper is vertically symmetrical). It will be understood that alternative lens blanks may utilize alternative tapering. The skilled artisan may adjust the positions from which to cut the right and left lenses such that the normal line of sight in the as-worn orientation is maintained substantially parallel to the optical centerline, regardless of the tapering symmetry.

Advantages

The present application thus provides an optically correct goggle, and particularly an optically correct double lens goggle such as is particularly useful for skiing applications. The illustrated embodiment minimizes fogging within the goggle in use, while at the same time providing minimal levels of astigmatism, power and prismatic distortion.

Moreover, a precise method of furnishing the correct correspondence between taper and the varying angle of incidence from the wearer's eye to the surface of a lens is provided. By recognizing a novel relationship among the wearer's line of sight and the form of taper, the present invention allows use of any of a variety of lens designs while minimizing astigmatism, power and prismatic distortion. For example, a designer may choose a desirable orientation and curvature for the lens, relative to a wearer's line of sight. The orientation and curvature may be chosen from a wide range of rake, wrap and proximity to a wearer's face. The form of taper and location of the lens profile on a theoretical shape or lens blank may then be chosen, by the method of the present invention, such that the prismatic distortion in the as-worn orientation is minimized.

Although the foregoing invention has been described in terms of certain preferred embodiments, other embodiments will become apparent to those of ordinary skill in the art in view of the disclosure herein. Accordingly, the present invention is not intended to be limited by the recitation of preferred embodiments, but is intended to be defined solely by reference to the appended claims.

We claim:

1. An optically corrected, non-prescription double lens goggle, comprising an inner lens having a first curved configuration and an outer lens having a second curved configuration, said inner and outer lenses supported within a goggle frame, said inner lens spaced behind said outer lens by an insulating space, at least one of said inner and outer lenses having a thickness tapered to reduce prismatic distortion through the goggle relative to an uncorrected double lens goggle with uniformly thick lenses separated by the insulating space and having the first and second curved configurations.

2. The goggle of claim 1, wherein the inner lens has a tapered thickness.

3. The goggle of claim 1, wherein both of the inner and outer lenses have tapered thicknesses.

4. The goggle of claim 1, further comprising a goggle frame configured to support the inner and outer lenses in an as-worn orientation on a wearer's head.

5. The goggle of claim 4, wherein an optical centerline of the inner and outer lenses is maintained substantially parallel to the wearer's normal lines of sight in the as-worn orientation.

6. A double lens goggle, comprising:
 a goggle frame configured to fit on a wearer's head in an as-worn orientation;
 a first curved unitary lens mounted to the goggle frame for extending across the wearer's left and right eyes in the as-worn orientation, the first lens having a first prismatic effect in the as-worn orientation; and a second curved unitary lens mounted to the goggle frame for extending across the wearer's left and right eyes in the as-worn orientation, the second lens spaced from the first lens to define an insulated space therebetween, the second lens having a second prismatic effect in the as-worn orientation, the second prismatic effect substantially compensating for the first prismatic effect.

7. A double lens goggle as in claim 6, wherein the first lens has a front surface and a rear surface, and at least one of the front surface and rear surface conforms to a portion of the surface of a toroid.

8. A double lens goggle as in claim 6, wherein the first lens has a curvature in the vertical direction, and a radius of the vertical curvature is within the range of from about 4.0 inches to 6.0 inches.

9. A double lens goggle as in claim 8, wherein the radius of the vertical curvature is within the range of from about 4.8 inches to 5.1 inches.

10. A double lens goggle as in claim 6, wherein the first lens has a curvature in the horizontal direction, and a radius of the horizontal curvature is within the range of from about 2.0 inches to 4.0 inches.

11. A double lens goggle as in claim 10, wherein the radius of the vertical curvature is within the range of from about 2.75 inches to 3.50 inches.

12. A double lens goggle as in claim 11, wherein the radius of the vertical curvature is within the range of from about 3.1 inches to 3.3 inches.

13. A double lens goggle as in claim 6, exhibiting no more than about $\frac{1}{8}$ diopter prismatic distortion and no more than about $\frac{1}{8}$ diopter refractive power in the as-worn orientation.

14. A double lens goggle as in claim 13, exhibiting no appreciable astigmatism in the as-worn orientation.

15. A double lens goggle as in claim 13, exhibiting no more than about $\frac{1}{16}$ diopter prismatic distortion and no more than about $\frac{1}{16}$ diopter refractive power in the as-worn orientation.

16. A double lens goggle as in claim 13, wherein at least one of the first and second lenses is mounted with a degree of rake in the as-worn orientation.

17. A double lens goggle as in claim 13, wherein each of the first and second lenses is raked to have a displacement of a lens optical centerline from the wearer's normal lines of sight from each eye of between about 0.1 inch and about 2.0 inches in the as-worn orientation.

18. A double lens goggle as in claim 17, wherein said displacement is between about 0.25 inch and about 0.75 inch in the as-worn orientation.

19. An optically correct ski goggle, comprising:

a unitary lens configured to extend across a wearer's normal lines of sight from the wearer's left and right eyes in an as-worn orientation, said lens including a convex surface facing a front side of the goggle and a concave surface facing a rear side of the goggle in the as-worn orientation, said lens exhibiting no more than about $\frac{1}{8}$ diopter prismatic distortion and no more than about $\frac{1}{8}$ diopter refractive power in an as-worn orientation; and a goggle frame supporting said lens upon the wearer's head in the as-worn orientation, the frame defining an enclosed space between the convex surface of said lens and the wearer's head, the enclosed space including a front vent communicating air from the front side of the goggle to the enclosed space in the as-worn orientation.

20. A ski goggle as defined in claim 19, further including a top vent at a top side of the goggle in the as-worn orientation.

21. A ski goggle as defined in claim 20, wherein said goggle frame comprises a front portion and a rear portion, the top vent defined between the front and rear portions of said frame.

22. A ski goggle as defined in claim 19, further including a second, inner unitary lens.

23. A ski goggle as defined in claim 19, wherein said lens exhibits no more than about $\frac{1}{16}$ diopter prismatic distortion and no more than about $\frac{1}{16}$ diopter refractive power in the as-worn orientation.

* * * * *